(12) United States Patent
Bojsen et al.

(10) Patent No.: US 6,967,035 B2
(45) Date of Patent: Nov. 22, 2005

(54) METHOD OF IMPROVING DOUGH AND BREAD QUALITY

(76) Inventors: Kirsten Bojsen, Bakkedal 5, 2900 Hellerup (DK); Charlotte Horsmans Poulsen, Langdalsvej 37, 8220 Braband (DK); Jorn Borch Soe, Orovænget 11, 8381 Tilst (DK)

(*) Notice: Subject to any disclaimer, the term of this patent is extended or adjusted under 35 U.S.C. 154(b) by 112 days.

(21) Appl. No.: 10/150,429

(22) Filed: May 17, 2002

(65) Prior Publication Data

US 2003/0175383 A1 Sep. 18, 2003

Related U.S. Application Data

(60) Provisional application No. 60/347,007, filed on Jan. 9, 2002.

(30) Foreign Application Priority Data

May 18, 2001 (GB) .............................. 0112226

(51) Int. Cl.$^7$ ................................. A21D 8/04
(52) U.S. Cl. .......................... 426/20; 426/18; 426/549; 426/653
(58) Field of Search .............................. 426/18, 19, 20, 426/61, 549, 552, 553, 653; 435/198

(56) References Cited

FOREIGN PATENT DOCUMENTS

| EP | 0 585 988 | 3/1996 |
|---|---|---|
| GB | 2 358 784 A | 8/2001 |
| WO | WO 94/04035 | 3/1994 |
| WO | WO 98/45453 | 10/1998 |
| WO | WO 00/32758 | 6/2000 |
| WO | WO 01/39602 | 6/2001 |
| WO | WO 02/00852 A2 | 1/2002 |
| WO | WO 02/03805 A1 | 1/2002 |
| WO | WO 02/65854 A2 | 8/2002 |
| WO | WO 02/66622 A2 | 8/2002 |

OTHER PUBLICATIONS

Marion D—Chapter 6, pp 131–167 of "*Interactions The Keys to Cereal Quality*" 1998 ISBN 0 913250-99-6 (ed. Hamer & Hoseney).
Conference May 6–8, 1999 in Santorini, Greece—Lipases & Lipids Structure, Function and Biotechnological Applications—Slides presented by Charlotte Poulsen.
Marion D et al.—pp 245–260 of Wheat Structure Biochemistry & Functionality (ed. Schofield JP) ISBN 085404777-8 published in 2000—(Proceedings of Conference organized by Royal Soc of Chemistry Food Chemistry Group held on Apr. 10–12, 1995, in Reading, UK).

Angelino S A G F et al. ed. The proceedings of the First European Symposium on Enzymes and Grain Processing. TNO Nutrition and Food Research Institute, Zeist, The Netherlands, 1997.

Matos et al., "*A novel patatin–like gene stimulated by drought stress encodes a galactolipid acyl hydrolase,*" Federation of European Biochemical Societies, published by Elsevier Science B.V., 2001.

Martinez et al., "*A pancreatic lipase with a phospholipase A1 activity: crystal structure of a chimeric pancreatic lipase–related protein 2 from guinea pig,*" Current Biology Ltd., Nov. 15, 1996, 4:1363–1374.

Cordle et al., "*The hydrophobic surface of colipase influences lipase activity at an oil–water interface,*" Journal of Lipid Research, vol. 39, 1998, 1759–1767.

Sahsah et al., "*Purification and characterization of soluble lipolytic acylhydrolase from Cowpea (Vigna unguiculata L.) leaves,*" Biochimica et Biophysica Acta 1215 (1994), 66–73.

O'Sullivan et al., *A Galactolipase Activity Associated with the Thylakoids of Wheat Leaves (Triticum aestivum* L.), J. Plant Physiol, vol. 131, pp. 393–404 (1987).

Carriere et al., "*Pancreatic Lipase Structure—Function Relationships by Domain Exchange,*" American Chemical Society—Biochemistry, 1997, 36, pp. 239–248.

Bornscheur, "*Lipase–catalyzed syntheses of monoacylglycerols,*" Enzyme Microb. Technol., 1995, vol. 17, Jul., pp. 578–586.

Krog, "*Dynamic and Unique Monoglycerides,*" Cereal Foods World, The American Association of Cereal Chemists, p. 10, Jan. 1979, vol. 24, No. 1, pp. 10–11.

Hou, "*pH dependence and thermostability of lipases from cultures from the ARS Culture Collection,*" Journal of Industrial Microbiology, Society for the Industrial Microbiology, 13 (1994), 242–248.

Villenueva et al., "*Lipase specificities: Potential application in lipid bioconversions,*" Inform, vol. 8, No. 6, (Jun. 1997).

*Primary Examiner*—Keith Hendricks
(74) *Attorney, Agent, or Firm*—Fay, Sharpe, Fagan, Minnich & McKee, LLP

(57) ABSTRACT

A method of preparing a flour dough, said method comprising adding to the dough components an enzyme that under dough conditions is capable of hydrolysing a glycolipid and a phospholipid, wherein said enzyme is incapable, or substantially incapable, of hydrolysing a triglyceride and/or a 1-monoglyceride, or a composition comprising said enzyme, and mixing the dough components to obtain the dough.

32 Claims, 13 Drawing Sheets

Figure 1:
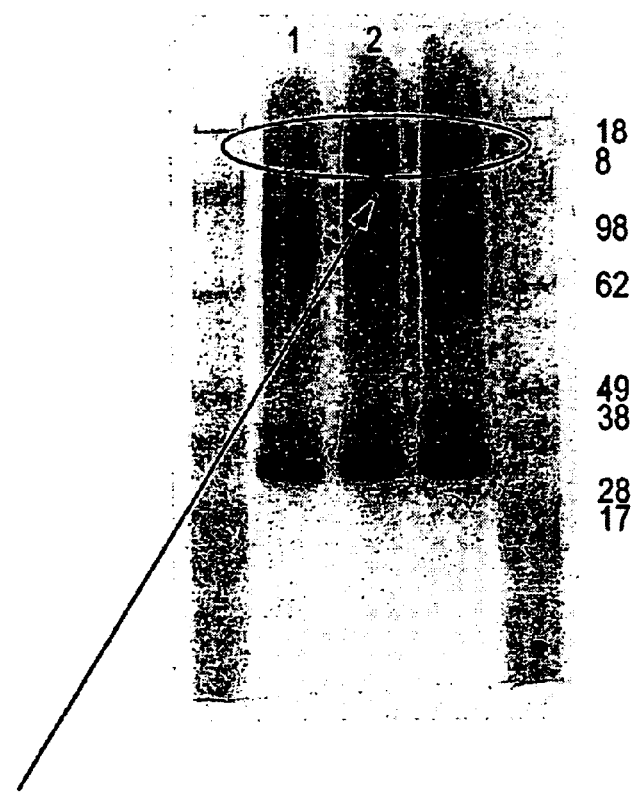

ACTIVITY STAINING, DGDG-PLATE
40°C, 18 HOURS

GALACTOLIPASE ACTIVITY

PROTEIN: COW PEA LIPASE  [GPMAW] 16/ 5/2002
FILE ORIGIN:  NO: 0
CLEAVAGE CONDITIONS: /K/R-\P  MASS FILE: CM-CYS

---

MASS SHOWN IS: AVERAGE

| NO | FROM- | TO | MASS | CH | B&B | HPLC | SEQ. |
|---|---|---|---|---|---|---|---|
| 1 | 1- | 9 | 934.09 | 1 | 2820 | 9.39 | MAATQTPSK |
| 2 | 10- | 27 | 1771.01 | -2 | -2070 | 23.25 | VDDGALITVLSIDGGGIR |
| 3 | 28- | 44 | 1841.23 | -1 | -7540 | 29.28 | GIIPGILLAFLESELQK |
| 4 | 45- | 51 | 716.75 | -1 | 2290 | 9.23 | LDGADAR |
| 5 | 52- | 86 | 3656.14 | -1 | -1710 | 27.25 | LADYFDVIAGTSTGGLVTAMLTAPNENNRPLYAAK |
| 6 | 87- | 89 | 374.44 | 0 | -380 | 6.68 | DIK |
| 7 | 90- | 98 | 1149.27 | 0 | -2210 | 17.71 | DFYLEHTPK |
| 8 | 99- | 114 | 1794.11 | 1 | -3010 | 24.71 | IFPQSSSWNLIATAMK |
| 9 | 115- | 115 | 146.19 | 1 | 460 | 1.09 | K |
| 10 | 116- | 117 | 231.26 | 1 | 1500 | 2.11 | GR |
| 11 | 118- | 127 | 1095.25 | 0 | 170 | 16.42 | SLMGPQYDGK |
| 12 | 128- | 131 | 559.67 | 2 | -1930 | 12.20 | YLHK |
| 13 | 132- | 134 | 386.50 | 1 | -1710 | 8.75 | LVR |
| 14 | 135- | 136 | 275.31 | 0 | 970 | 1.51 | EK |
| 15 | 137- | 141 | 531.61 | 1 | 800 | 5.45 | LGNTK |
| 16 | 142- | 157 | 1010.13 | 0 | -5040 | 22.49 | LEHTLTNVVIPAFDIK |
| 17 | 158- | 170 | 1478.72 | 1 | -2320 | 22.19 | NLQPAIFSSFQVK |
| 18 | 171- | 171 | 146.19 | 1 | 460 | 1.09 | K |
| 19 | 172- | 201 | 3368.74 | 1 | -2990 | 30.83 | RPYLNAALSDICISTSAAPTYLPAHCFETK |
| 20 | 202- | 208 | 740.82 | 1 | 970 | 9.94 | TSTASFK |
| 21 | 209- | 234 | 2673.00 | -3 | 590 | 21.46 | FDLVDGGVAANNPALVAMAEVSNEIR |
| 22 | 235- | 243 | 965.01 | 0 | 2830 | 12.66 | NEGSCASLK |
| 23 | 244- | 250 | 875.08 | 2 | -2110 | 14.08 | VKPLQYK |
| 24 | 251- | 251 | 146.19 | 1 | 460 | 1.09 | K |
| 25 | 252- | 267 | 1803.08 | 1 | -1100 | 23.26 | FLVISLGTGSQQHEMR |
| 26 | 268- | 272 | 582.62 | 0 | 670 | 7.13 | YSADK |
| 27 | 273- | 313 | 4353.84 | 0 | -4340 | 35.98 | ASTWGLVGWLSSSGGTPLIDVFSHASSDMVDFHISSVFQAR |
| 28 | 314- | 321 | 1030.11 | 1 | 1280 | 12.48 | HAEQNYLR |
| 29 | 322- | 340 | 1977.11 | -4 | 1650 | 18.47 | IQDDTLTGDLGSVDVATEK |
| 30 | 341- | 354 | 1481.76 | 0 | -2350 | 18.34 | NLNGLVQVAEALLK |
| 31 | 355- | 359 | 557.70 | 2 | 420 | 4.85 | KPVSK |
| 32 | 360- | 363 | 514.63 | 1 | -1520 | 10.70 | INLR |
| 33 | 364- | 381 | 1939.07 | -2 | 3980 | 14.73 | TGIHEPVESNETNAEALK |
| 34 | 382- | 382 | 174.21 | 1 | 690 | 1.41 | R |
| 35 | 383- | 386 | 463.54 | 1 | 390 | 9.62 | FAAR |
| 36 | 387- | 391 | 616.68 | 1 | 1320 | 7.10 | LSNQR |
| 37 | 392- | 392 | 174.21 | 1 | 690 | 1.41 | R |
| 38 | 393- | 394 | 321.38 | 1 | -830 | 8.94 | FR |
| 39 | 395- | 395 | 146.19 | 1 | 460 | 1.09 | K |
| 40 | 396- | 400 | 552.59 | 0 | 770 | 10.45 | SQTFA |

FIG. 13

SEQUENCE LISTING

```
<160> NUMBER OF SEQ ID NOS: 12
<210> SEQ ID NO 1
<211> LENGTH: 400
<212> TYPE: PRT
<213> ORGANISM: Vigna unguiculata

<400> SEQUENCE: 1

Met Ala Ala Thr Gln Thr Pro Ser Lys Val Asp Asp Gly Ala Leu Ile
1               5                   10                  15

Thr Val Leu Ser Ile Asp Gly Gly Ile Arg Gly Ile Ile Pro Gly
            20                  25                  30

Ile Leu Leu Ala Phe Leu Glu Ser Glu Leu Gln Lys Leu Asp Gly Ala
        35                  40                  45

Asp Ala Arg Leu Ala Asp Tyr Phe Asp Val Ile Ala Gly Thr Ser Thr
    50                  55                  60

Gly Gly Leu Val Thr Ala Met Leu Thr Ala Pro Asn Glu Asn Asn Arg
65                  70                  75                  80

Pro Leu Tyr Ala Ala Lys Asp Ile Lys Asp Phe Tyr Leu Glu His Thr
                85                  90                  95

Pro Lys Ile Phe Pro Gln Ser Ser Ser Trp Asn Leu Ile Ala Thr Ala
            100                 105                 110

Met Lys Lys Gly Arg Ser Leu Met Gly Pro Gln Tyr Asp Gly Lys Tyr
```

-continued

```
            115                 120                 125
Leu His Lys Leu Val Arg Glu Lys Leu Gly Asn Thr Lys Leu Glu His
    130                 135                 140

Thr Leu Thr Asn Val Val Ile Pro Ala Phe Asp Ile Lys Asn Leu Gln
145                 150                 155                 160

Pro Ala Ile Phe Ser Ser Phe Gln Val Lys Lys Arg Pro Tyr Leu Asn
                165                 170                 175

Ala Ala Leu Ser Asp Ile Cys Ile Ser Thr Ala Ala Pro Thr Tyr
                180                 185                 190

Leu Pro Ala His Cys Phe Glu Thr Lys Thr Ser Thr Ala Ser Phe Lys
                195                 200                 205

Phe Asp Leu Val Asp Gly Gly Val Ala Ala Asn Asn Pro Ala Leu Val
    210                 215                 220

Ala Met Ala Glu Val Ser Asn Glu Ile Arg Asn Gly Ser Cys Ala
225                 230                 235                 240

Ser Leu Lys Val Lys Pro Leu Gln Tyr Lys Lys Phe Leu Val Ile Ser
                245                 250                 255

Leu Gly Thr Gly Ser Gln Gln His Glu Met Arg Tyr Ser Ala Asp Lys
                260                 265                 270

Ala Ser Thr Trp Gly Leu Val Gly Trp Leu Ser Ser Gly Gly Thr
                275                 280                 285

Pro Leu Ile Asp Val Phe Ser His Ala Ser Ser Asp Met Val Asp Phe
    290                 295                 300

His Ile Ser Ser Val Phe Gln Ala Arg His Ala Glu Gln Asn Tyr Leu
305                 310                 315                 320

Arg Ile Gln Asp Asp Thr Leu Thr Gly Asp Leu Gly Ser Val Asp Val
                325                 330                 335

Ala Thr Glu Lys Asn Leu Asn Gly Leu Val Gln Val Ala Glu Ala Leu
                340                 345                 350

Leu Lys Lys Pro Val Ser Lys Ile Asn Leu Arg Thr Gly Ile His Glu
                355                 360                 365

Pro Val Glu Ser Asn Glu Thr Asn Ala Glu Ala Leu Lys Arg Phe Ala
    370                 375                 380

Ala Arg Leu Ser Asn Gln Arg Arg Phe Arg Lys Ser Gln Thr Phe Ala
385                 390                 395                 400
```

<210> SEQ ID NO 2
<211> LENGTH: 5331
<212> TYPE: DNA
<213> ORGANISM: Vigna unguiculata

<400> SEQUENCE: 2

```
caaattctat ataaaatata atacattagg aagttagaaa atacttgacc tactctccaa    60
ttatttgatt cacgttcaaa atatatcatt acgattctag attaataaag attcctataa   120
agtttcaaat cacaaatgtg accattcaat atctcacatg caaccaaaat aaggaaaaag   180
ccttaagttt aaaaaataaa taaaagtttt actcaaaacc aaaacttaat aagataaact   240
tttcttatat tctgttaaat tttattcccc atactttaat aaaagaaagg ataagaaaca   300
actactttt atttacttt gtatttata gagataaaa agtttagata attgaaaagt       360
gaattagttt tacattatat ataactttta catactaaaa catttatttt tgttttaaat   420
taaagaaagg tacttacact agaaataacg tttataaatg aatgaaaatt acattcaatt   480
tcttaaaagt actgtgaata gaaaatgat aacaagaag aaaatatat agtgaattat      540
```

-continued

```
attacaagaa aaaaaaagtt gtcaattaat tattaataca ttgcatcaat aataaataaa    600
ggttctcatt tttgtagtga aatctcaaat aagttttctc atttttattt gactcaattg    660
agttactaat ttggaaaatt cattgcaatt agatcatttt cgttagtact acactagcga    720
tgttaactat gtgtcatgtg tcagcaagtg atttttttta aattttttt gaaaaaaata    780
aaaaaaaatt atcatgtgtt aatctgacat tgtgtcacat gttagagata atgtgatgtg    840
acagtaatag taccacatgt cactattgaa tgtgaaaagt cttaatataa tccttgtatt    900
tattattttg tttcaattta acattttttt aaacataaaa caatttaatt aattttttaa    960
atttcatatt ttctaaatat tttagataag taaaaaataa taataatacg attaaacctt   1020
aattttgtac tttacaacta ctatttgatg gttatgcttt taagttgtgg ttgaaatagt   1080
ggtgaagagc atacgtgaat atgacaaata aagaaacaaa cgcaattatg acattcttat   1140
cctttctaa gtattttctt ataattacag tcttttgaaa ttattgtgta tgaaattaaa   1200
gtaggtatgt gggaatgtga caataataat aactaaggag actctgaaaa gttctgagaa   1260
tttaatgaat taattataat ttaaacaagt cagacaagaa aattataaag ttctctaacc   1320
tagtacgtgc ctcataaaat aatagtcatg ctattataaa ataattaatt atggtgggtg   1380
gaatgttcat tgacacaatt atttagatat tttctcattg actcattgac acatggttca   1440
ttgctatcca tctattacca atgaatatta ccttttgtcg tctatgataa tttattttta   1500
taattttaat actctatcaa agtaaaaata ttgtccagga aaaatgggtt ttattaataa   1560
ttaattgaag gtgaattaac tatactaaat attataccaa tggataatta cattgcaaaa   1620
gaatacccttt gtagtatttt gaaatatgat attttaaagt aacttgttgt tcattaaaaa   1680
attaaaaatt taaatataag tttaagtctt acactaaaaa aaataaaaaa atataaagtt   1740
gagtatcata taaagatgaa aactcataaa acatattaga gttgaaggtt aatagtctat   1800
ttagacaaat ttttgtatcg agaaagaaat accgatggga catactcatg ggataaaatca   1860
aaactaagtg aaaataaaat ttgaggtaaa gaaaatacat atttaataaa tttaaaagtg   1920
aaatttttaa tgtgtgtcca aaatatttgt taaataataa taaacatatt ttacatcacc   1980
taatccatgc gtttttcatc ggatttacgg gccggtccga cgggccagat cctaattgtc   2040
accccttatg tattttatat atggtatata tgactaacat gagaaaatgt gaccgttaaa   2100
agcagagttt taatcaaaca taagtaaaaa tgagtatagt taaaccaaaa cttgatttac   2160
catatataac tcataacaga gactttaaca cagatctgca aaccttccta gtatgtacac   2220
tgcaaaaaca agggaacaca aaggttgccc tacgcattca atctcattaa tctctgtggt   2280
ccaaaacact ttgtgtgtat atgatttgaa tattactatt atacatccaa caatagtaat   2340
tcttgtcttt tgtgtctata tgatttgaac gctagtatta cattctctat caactcttcc   2400
atacatttat tgatcgcccc accatcaaaa aaccataact aacacgtgaa aactgataaa   2460
aataacgtca gcatagaagt tctgaacgtt caatattatt cacagaaaaa agatattatc   2520
catttcgacg ttttttgtggt aattaactta acatggtgct aagattttgg tataggagat   2580
gatgttatat aggttacctt aattatgatt gaagtgagtg aagaattctt attcattgaa   2640
agtgttttta actgaggttt tagacaaact atacctaatt ttactagttt aatccctctt   2700
aagaaaaaaa aaccaactcc tgaacacca acaaacacca taagtaacac gtttgaaaac   2760
ggactaaaat aatgttgaag ctctcgacaa ttaaataggt ttcatggaaa catattatcc   2820
atttccctgt ttttgtggca actaattgaa cacgctaaaa acaagacaag taaactcacc   2880
aacatcttca ctctttacac ggtttggctt tatatataaa tatgcagttt ctcctcatca   2940
```

```
aatcaaccca tgaaaaccag attttcctga ataagtttgt gtaagagttc agtagttttc    3000
tttgctcttt cctaagttca ttccatctct ctttctttct ctttctttct cactgtgtgt    3060
gtctctctct ttctctttga cttagtaagt catcaattca gatccatggc agcaactcaa    3120
actccaagca aagttgatga tggagcactg attactgtgc tgagtattga tggtggtggc    3180
attcgtggaa tcattcccgg aattttgctt gctttcctcg aatcagaact tcaggtaata    3240
ataatctatg gtaaccaaga gaaaacgttt atatgtaaat taatgcagga aagtaactaa    3300
taatggtgca tatgcagaaa ctggatggtg ctgatgcaag actcgcagat tactttgatg    3360
tgattgcagg aacaagcacc ggtggattag tcactgcaat gctcactgct ccaaatgaaa    3420
ataatcgacc cttgtatgca gccaaagata taaaggattt ctaccttgag catacccaa    3480 aaatcttccc gcagagtagg taaataccac actttacacc ataaacttcg taccaaatca    3540
ttcaaatcta aatacacact gtgtactaat ttacagtgtg attttttccc aaatacagta    3600
gctggaattt gattgcaaca gcgatgaaga aaggcagaag tctgatggga ccacagtacg    3660
atggcaagta tttacacaag ctcgttaggg aaaaactagg gaacacaaaa ttggaacaca    3720
cattaaccaa tgtcgttatc ccagcatttg atatcaaaaa ccttcaaccc gccatctttt    3780
ccagcttcca ggttcacccc tcctcctctc aattgcaaaa agtcactcac ttgaaagcaa    3840
aaattgcagc ttttgttt tctctaacga aattattact ctcgaatatg atgtcacagg    3900
tgaagaagag gccatatttg aatgcggcgt tgtctgatat atgcatttca acctcggcag    3960
caccaaccta tctcccagct cattgctttg aaactaaaac cagcactgct agtttcaaat    4020
tcgaccttgt agatggtggt gtagcagcaa ataacccggt attgtattat acagtctcag    4080
aactaatctt aatcattcat aacataatca cacacacaaa cactataatt aacaagtata    4140
aatttaatcg ataacagaag aaggtgatag atatgttata atctggcatt ttccaggctc    4200
tggtggcgat ggcagaagtg tcgaacgaaa tccgcaatga agggtcatgt gcaagcttga    4260
aagtaaaacc gttgcaatac aaaaagttt tggtgatatc gttgggaaca ggttctcagc    4320
aacacgaaat gagatacagt gctgataagg catcgacatg gggccttgtg ggttggcttt    4380
cctcctccgg tggcactcct ctcatcgatg ttttcagcca tgctagttct gacatggttg    4440
atttccacat ctcctccgtt ttccaagcac gccatgctga acaaaactac ctccgaatcc    4500
aggttctttc cgaacatata tataaacatc ttcaatgatt ctcgtgcttg caaatgaaaa    4560
ctcatgagtt caatctttat attcaaattt gcaggatga tactttaact ggggacttag    4620
gttcggtgga cgtggccacg gagaagaatc tgaatggcct cgtccaagtt gcggaagcat    4680
tgttaaagaa accagtttca aagattaact tgaggaccgg tattcatgaa cctgttgagt    4740
ctaacgaaac caacgcagaa gccttgaaga ggtatatata tatcaaaacc ctactcatac    4800
acacacatga taatggaaag aatttaagaa aaactgtgta agaaattaaa gtatatatac    4860
aataaaaaca tcatgtgttc atcgtactaa tgttttatta acaacgtatt ttttatcaaa    4920
cgaaatccat atatgagttg taacttcttc gaatcacagt ttcacgttca cttcacttca    4980 ctatttttt atatcaggtt tgcggcacga ctatccaacc agaggagatt tcggaaatct    5040
caaacgtttg cgtagaatgg gaatcttcga aagatgaaga tatacgagac acgtgttgct    5100
tggccaatat gataaatgat tggtgtagtg tttatcttaa ttttatatat ttttctttat    5160
atttcgtagt gttcattaca gtgaagatat attcattgta ctgaatcaca ataattagtg    5220
tccctacaat attaaatctc atgtgctgta aacgctttgt gtttctttgt tttcatttac    5280
```

```
caatgtaatc agtttggttc actatattgt ctctaattca ttttattta a        5331
```

```
<210> SEQ ID NO 3
<211> LENGTH: 297
<212> TYPE: PRT
<213> ORGANISM: Aspergillus tubingensis

<400> SEQUENCE: 3
```

```
Met Phe Ser Gly Arg Phe Gly Val Leu Leu Thr Ala Leu Ala Ala Leu
1               5                   10                  15

Gly Ala Ala Ala Pro Ala Pro Leu Ala Val Arg Ser Val Ser Thr Ser
            20                  25                  30

Thr Leu Asp Glu Leu Gln Leu Phe Ala Gln Trp Ser Ala Ala Ala Tyr
        35                  40                  45

Cys Ser Asn Asn Ile Asp Ser Lys Asp Ser Asn Leu Thr Cys Thr Ala
    50                  55                  60

Asn Ala Cys Pro Ser Val Glu Glu Ala Ser Thr Thr Met Leu Leu Glu
65                  70                  75                  80

Phe Asp Leu Thr Asn Asp Phe Gly Gly Thr Ala Gly Phe Leu Ala Ala
                85                  90                  95

Asp Asn Thr Asn Lys Arg Leu Val Val Ala Phe Arg Gly Ser Ser Thr
            100                 105                 110

Ile Glu Asn Trp Ile Ala Asn Leu Asp Phe Ile Leu Glu Asp Asn Asp
        115                 120                 125

Asp Leu Cys Thr Gly Cys Lys Val His Thr Gly Phe Trp Lys Ala Trp
    130                 135                 140

Glu Ser Ala Ala Asp Glu Leu Thr Ser Lys Ile Lys Ser Ala Met Ser
145                 150                 155                 160

Thr Tyr Ser Gly Tyr Thr Leu Tyr Phe Thr Gly His Ser Leu Gly Gly
                165                 170                 175

Ala Leu Ala Thr Leu Gly Ala Thr Val Leu Arg Asn Asp Gly Tyr Ser
            180                 185                 190

Val Glu Leu Tyr Thr Tyr Gly Cys Pro Arg Ile Gly Asn Tyr Ala Leu
        195                 200                 205

Ala Glu His Ile Thr Ser Gln Gly Ser Gly Ala Asn Phe Arg Val Thr
    210                 215                 220

His Leu Asn Asp Ile Val Pro Arg Val Pro Pro Met Asp Phe Gly Phe
225                 230                 235                 240

Ser Gln Pro Ser Pro Glu Tyr Trp Ile Thr Ser Gly Asn Gly Ala Ser
                245                 250                 255

Val Thr Ala Ser Asp Ile Glu Val Ile Glu Gly Ile Asn Ser Thr Ala
            260                 265                 270

Gly Asn Ala Gly Glu Ala Thr Val Ser Val Val Ala His Leu Trp Tyr
        275                 280                 285

Phe Phe Ala Ile Ser Glu Cys Leu Leu
    290                 295
```

```
<210> SEQ ID NO 4
<211> LENGTH: 894
<212> TYPE: DNA
<213> ORGANISM: Aspergillus tubingensis

<400> SEQUENCE: 4
```

```
atgttctctg gacggtttgg agtgcttttg acagcgcttg ctgcgctggg tgctgccgcg      60
ccggcaccgc ttgctgtgcg gagtgtctcg acttccacgt tggatgagtt gcaattgttc     120
```

```
gcgcaatggt ctgccgcagc ttattgctcg aataatatcg actcgaaaga ctccaacttg      180
acatgcacgg ccaacgcctg tccatcagtc gaggaggcca gtaccacgat gctgctggag      240
ttcgacctga cgaacgactt tggaggcaca gccggtttcc tggccgcgga caacaccaac      300
aagcggctcg tggtcgcctt ccggggaagc agcacgattg agaactggat tgctaatctt      360
gacttcatcc tggaagataa cgacgacctc tgcaccggct gcaaggtcca tactggtttc      420
tggaaggcat gggagtccgc tgccgacgaa ctgacgagca agatcaagtc tgcgatgagc      480
acgtattcgg gctatacccT atacttcacc gggcacagtt tgggcggcgc attggctacg      540
ctgggagcga cagttctgcg aaatgacgga tatagcgttg agctgtacac ctatggatgt      600
cctcgaatcg gaaactatgc gctggctgag catatcacca gtcagggatc tggggccaac      660
ttccgtgtta cacacttgaa cgacatcgtc ccccgggtgc cacccatgga ctttggattc      720
agtcagccaa gtccggaata ctggatcacc agtggcaatg gagccagtgt cacggcgtcg      780
gatatcgaag tcatcgaggg aatcaattca acggcgggaa atgcaggcga agcaacggtg      840
agcgttgtgg ctcacttgtg gtacttttt gcgatttccg agtgcctgct ataa           894
```

<210> SEQ ID NO 5
<211> LENGTH: 51
<212> TYPE: DNA
<213> ORGANISM: Artificial Sequence
<220> FEATURE:
<221> NAME/KEY: primer_bind
<222> LOCATION: (1)..(51)
<223> OTHER INFORMATION: lipase primer JOM1

<400> SEQUENCE: 5

```
caagctatac caagcataca atcaactcca aaatgttctc tggacggttt g             51
```

<210> SEQ ID NO 6
<211> LENGTH: 29
<212> TYPE: DNA
<213> ORGANISM: Artificial Sequence
<220> FEATURE:
<221> NAME/KEY: primer_bind
<222> LOCATION: (1)..(29)
<223> OTHER INFORMATION: lipase primer JOM2

<400> SEQUENCE: 6

```
caaacctctg gcgaagaagt ccaaagctg                                       29
```

<210> SEQ ID NO 7
<211> LENGTH: 21
<212> TYPE: DNA
<213> ORGANISM: Artificial Sequence
<220> FEATURE:
<221> NAME/KEY: primer_bind
<222> LOCATION: (1)..(21)
<223> OTHER INFORMATION: lipase primer JOM3

<400> SEQUENCE: 7

```
gctcgtggtc gccttccggg g                                               21
```

<210> SEQ ID NO 8
<211> LENGTH: 19
<212> TYPE: DNA
<213> ORGANISM: Artificial Sequence
<220> FEATURE:
<221> NAME/KEY: primer_bind
<222> LOCATION: (1)..(19)
<223> OTHER INFORMATION: lipase primer JOM4

<400> SEQUENCE: 8

```
gccggtgcag aggtcgtcg                                                      19
```

<210> SEQ ID NO 9
<211> LENGTH: 22
<212> TYPE: DNA
<213> ORGANISM: Artificial Sequence
<220> FEATURE:
<221> NAME/KEY: primer_bind
<222> LOCATION: (1)..(22)
<223> OTHER INFORMATION: lipase primer JOM5

<400> SEQUENCE: 9

```
cctcgaatcg gaaactatgc gc                                                  22
```

<210> SEQ ID NO 10
<211> LENGTH: 20
<212> TYPE: DNA
<213> ORGANISM: Artificial Sequence
<220> FEATURE:
<221> NAME/KEY: primer_bind
<222> LOCATION: (1)..(20)
<223> OTHER INFORMATION: lipase primer JOM13

<400> SEQUENCE: 10

```
tgtcacggcg tcggatatcg                                                     20
```

<210> SEQ ID NO 11
<211> LENGTH: 20
<212> TYPE: DNA
<213> ORGANISM: Artificial Sequence
<220> FEATURE:
<221> NAME/KEY: primer_bind
<222> LOCATION: (1)..(20)
<223> OTHER INFORMATION: lipase primer JOM14

<400> SEQUENCE: 11

```
ctcatccaac gtggaagtcg                                                     20
```

<210> SEQ ID NO 12
<211> LENGTH: 406
<212> TYPE: PRT
<213> ORGANISM: wheat derivative

<400> SEQUENCE: 12

Met Cys Ser Gln Ala Asp Pro Thr Leu Thr Cys Pro Pro Ser Gln
 1               5                  10                  15

Gly Arg Leu Ile Thr Val Leu Ser Ile Asp Gly Gly Ile Arg Gly
            20                  25                  30

Leu Ile Pro Ser Thr Ile Leu Ala Cys Leu Glu Ser Lys Leu Gln Glu
        35                  40                  45

Leu Asp Gly Pro Asp Ala Arg Ile Ala Asp Tyr Phe Asp Val Ile Ala
    50                  55                  60

Gly Thr Ser Thr Gly Ala Leu Val Thr Ser Met Leu Ala Ala Pro Gly
65                  70                  75                  80

Glu Asn Lys Arg Pro Leu Phe Glu Ala Lys Asp Ile Asn Lys Phe Tyr
                85                  90                  95

Leu Asp Asn Gly Pro Lys Ile Phe Pro Gln Lys Gly Trp Gly Val Leu
            100                 105                 110

Thr Pro Met Ala Asn Leu Phe Gly Ala Val Thr Gly Pro Lys Tyr Asp
        115                 120                 125

Gly Lys Phe Leu His Asp Lys Ile Lys Ser Leu Thr Asn Asp Val Thr
    130                 135                 140

-continued

```
Val Ala Asp Thr Val Thr Asn Ile Ile Val Pro Thr Phe Asp Ile Lys
145                 150                 155                 160

Tyr Leu Gln Pro Ile Ile Phe Asn Thr Tyr Glu Ala Lys Val Asp Pro
            165                 170                 175

Leu Lys Asn Ala His Leu Ser Asp Ile Cys Ile Ser Thr Ser Ala Ala
            180                 185                 190

Pro Thr Tyr Phe Pro Ala His Tyr Phe Thr Thr Arg Asp Pro Ala Gly
        195                 200                 205

Lys Leu Pro Asp Arg Glu Tyr His Leu Ile Asp Gly Val Ala Ala
        210                 215                 220

Asn Asn Pro Thr Met Ala Ala Met Ser Met Ile Thr Lys Glu Val Leu
225                 230                 235                 240

Arg Arg Asn Pro Asp Phe Thr His Gly Lys Pro Ala Glu Tyr Gly Asn
            245                 250                 255

Tyr Leu Ile Ile Ser Ile Gly Thr Gly Ser Ala Lys Met Ala Glu Lys
            260                 265                 270

Tyr Thr Ala Pro Asp Cys Ala Lys Trp Gly Val Leu Arg Trp Leu Tyr
        275                 280                 285

Asp Gly Gly Phe Thr Pro Leu Ile Asp Ile Phe Ser His Ala Ser Ala
        290                 295                 300

Asp Met Val Asp Ile Gln Ala Ser Val Leu Phe Gln Val Leu Asp Cys
305                 310                 315                 320

Thr Lys Ser Tyr Val Arg Ile Gln His Ala Glu Leu Thr Gly Glu Met
            325                 330                 335

Ala Ser Val Tyr Val Ser Thr Ser Lys Ser Leu Asn Gly Phe Ile Ser
            340                 345                 350

Val Gly Lys Ala Leu Leu Lys Lys Gln Val Cys Lys Val Asn Val Glu
        355                 360                 365

Thr Gly Lys Asn Glu Pro Asp Leu Glu Arg Gly Ala Tyr Glu Glu Glu
        370                 375                 380

Leu Ala Arg Phe Val Arg Met Leu Ser Lys Glu Arg Lys Ala Arg Lys
385                 390                 395                 400

Glu Ala Tyr Lys Leu Val
                405
```

METHOD OF IMPROVING DOUGH AND BREAD QUALITY

This application claims benefit of 60/347,007 filed on Jan. 9, 2002.

FIELD OF THE INVENTION

The present invention relates to dough manufacture and flour dough based products and in particular, but not exclusively, to improving the strength and machinability of doughs and the volume, softness and crumb structure of bread and other baked products.

TECHNICAL BACKGROUND

Additives are widely used within the food industry in order to improve the quality of the food product. One of the most widely used food additives is the emulsifier and in particular monoglyceride.

Monoglyceride was originally produced as a mixture of mono-, di- and triglycerides. However, later technology was developed to produce highly purified monoglyceride by molecular distillation. Monoglyceride is traditionally produced by a glycerolysis reaction, wherein triglyceride and glycerol are reacted at high temperature above 200° C. using alkaline catalysts.

As an alternative to using alkaline catalysts and high temperatures many attempts have been made to use enzymes such as lipases in the production of monoglycerides. In a review article, Bornscheuer (Enzyme and Microbial Technology 17:578–585, 1995) mentions the enzymatic glycerolysis of triglycerides in the presence or absence of solvents and that monoglyceride can be produced by enzymatic glycerolysis in a solid phase.

Monoglyceride can be used as an emulsifier for many food applications. Within the baking industry, monoglyceride has been used to improve bread softness by complexing with starch and thereby retarding the crystallisation of amylopectin and the onset of bread staling.

Lipases (E.C. 3.1.1.3) have also been used directly in bread production. For instance, in EP 0 585 988 it is claimed that lipase addition to dough resulted in an improvement in the antistaling effect. It is suggested that a lipase obtained from *Rhizopus arrhizus* when added to dough can improve the quality of the resultant bread when used in combination with shortening/fat. WO94/04035 teaches that an improved softness can be obtained by adding a lipase to dough without the addition of any additional fat/oil to the dough. Castello, P. ESEGP 89–10 December 1999 Helsinki, shows that exogenous lipases can modify bread volume. Thus, lipases (E.C. 3.1.1.3) which hydrolyse triacylglycerols were known to be advantageous for use in the baking industry.

It has been shown in WO 98/45453 that the level of monoglyceride in doughs treated with lipase only increases very slightly, as the lipase added to the dough easily degrades monoglyceride to glycerol and free fatty acids. This is explained by the fact that lipases recognise the fatty acid part of the molecule in the active site and as monoglycerides and diglycerides are more orientated at the interface where the lipase is active, monoglycerides and diglycerides are easily degraded during lipase addition to a matrix containing fat/oil emulsions. Even with regard to 1.3 specific lipases, which only hydrolyse the fatty acids of a triglyceride in the 1 and 3 position leaving 2-monoglyceride as the reaction product, the resultant 2-monoglyceride easily rearranges to 1-monoglyceride, which can be hydrolysed by 1.3 specific lipases.

During enzymatic degradation of triglycerides by conventional lipases monoglycerides, diglycerides, free fatty acids and glycerol are formed.

Typically, the increase in monoglycerides in dough treated with one or more lipases is less than 0.1% (based on flour weight) with or without added fat or oil. However, the conventional dosage of monoglyceride required in dough to result in an improvement in, for instance, softness of the resultant bread is typically about 0.3–0.8% based on flour weight (Krog, N. Cereal Food World, 24, 10, 1979). Thus, any beneficial effect of adding conventional lipases to dough, as suggested in EP 0 585 988 and WO94/04035, is not a result of an increased monoglyceride content alone.

Some lipases in addition to having a triglyceride hydrolysing effect, are capable of hydrolysing polar lipids such as glycolipids, e.g. digalactosyldiglyceride (DGDG), and phospholipids (see for instance WO01/39602).

The substrate for lipases in wheat flour is 2–3% endogenous wheat lipids, which are a complex mixture of polar and non-polar lipids. The polar lipids can be divided into glycolipids and phospholipids. These lipids are built up of glycerol esterified with two fatty acids and a polar group. The polar group contributes to surface activity of these lipids. Enzymatic cleavage of one of the fatty acids in these lipids leads to lipids with a much higher surface activity. It is well known that emulsifiers, such as DATEM, with high surface activity are very functional when added to dough.

It has been found, however, that the use of lipases (E.C. 3.1.1.3) in dough may under certain conditions have detrimental consequences, such as the production of off-flavours, a detrimental impact on yeast activity, and/or a negative effect on bread volume. The negative effect on bread volume is often called overdosing. Overdosing can lead to a decrease in gluten elasticity which results in a dough which is too stiff and thus results in reduced volumes. In addition, or alternatively, such lipases can degrade shortening, oil or milk fat added to the dough.

SUMMARY ASPECT

A seminal finding of the present invention is that, surprisingly, the use of an enzyme, which under dough conditions is capable of hydrolysing a glycolipid and a phospholipid, but which is incapable, or substantially incapable, of hydrolysing a triglyceride and/or a 1-monoglyceride, is advantageous, and overcomes the disadvantages associated with the use of lipases (E.C. 3.1.1.3) which are capable of hydrolysing non-polar lipids in a dough.

DETAILED ASPECTS

The present invention provides in a first aspect a method of preparing a flour dough, said method comprising adding to the dough components an enzyme that under dough conditions is capable of hydrolysing a glycolipid and a phospholipid, wherein said enzyme is incapable, or substantially incapable, of hydrolysing a triglyceride and/or a 1-monoglyceride, and mixing the dough components to obtain the dough.

In a second aspect of the present invention, there is provided a method of preparing a dough or baked product prepared from a dough comprising:

(a) testing at least one enzyme for its hydrolytic activity towards a triglyceride, a 1-monoglyceride, a phospholipid and a glycolipid;

(b) selecting an enzyme having hydrolytic activity towards a phospholipid and a glycolipid and having no, or substantially no, hydrolytic activity towards a triglyceride and/or a 1-monoglyceride; and (c) adding the selected enzyme to the dough.

The present invention provides in a third aspect a dough improving composition comprising an enzyme having hydrolytic activity towards a phospholipid and a glycolipid and having no, or substantially no, hydrolytic activity towards a triglyceride and/or a 1-monoglyceride and, optionally, a further dough component.

In a fourth aspect, the present invention provides a dough obtainable by the method according to the present invention.

In a fifth aspect, the present invention provides a dough obtained by the method according to the present invention.

In a sixth aspect, the present invention provides a baked product obtainable by baking a dough according to the present invention.

In a seventh aspect, the present invention provides a baked product obtained by baking a dough according to the present invention.

The present invention further provides, in an eighth aspect, a noodle product made from a dough according to the present invention.

In a ninth aspect, the present invention provides a pasta product made from a dough according to the present invention.

In an tenth aspect, the present invention provides a method of preparing a dough improving composition wherein an enzyme having hydrolytic activity towards a phospholipid and a glycolipid and having no, or substantially no, hydrolytic activity towards a triglyceride and/or a 1-monoglyceride is, optionally, admixed with a further dough component.

In an eleventh aspect, a method of selecting an enzyme according to the present invention may comprise the steps of:
(a) testing at least one enzyme for its hydrolytic activity towards a triglyceride, a 1-monoglyceride, a phospholipid and a glycolipid;
(b) selecting an enzyme having hydrolytic activity towards a phospholipid and a glycolipid and having no, or substantially no, hydrolytic activity towards a triglyceride and/or a 1-monoglyceride.

The present invention provides in a twelfth aspect thereof a method of preparing or developing an enzyme having hydrolytic activity towards a phospholipid and a glycolipid and having no, or substantially no, hydrolytic activity towards a triglyceride and/or a 1-monoglyceride, comprising:
(a) selecting a lipase having hydrolytic activity towards a phospholipid, a glycolipid and a triglyceride and/or a 1-monoglyceride,
(b) modifying by insertion, deletion or substitution of at least one amino acid in the amino acid sequence, typically near or in the active site, so as to alter the activity of the lipase in such a way that the lipase is modified to have no, or substantially no, activity against a triglyceride and/or a 1-monoglyceride.

In a thirteenth aspect, the present invention provides the use of an enzyme that under dough conditions is capable of hydrolysing a glycolipid and a phospholipid, wherein said enzyme is incapable, or substantially incapable, of hydrolysing a triglyceride and/or a 1-monoglyceride, in the preparation of a dough to provide a dough with increased bread volume and/or increased gluten strength as compared with a dough without said enzyme.

In a fourteenth aspect, the present invention provides a method for removing polar lipids from an edible oil, said method comprising adding to an edible oil an enzyme that is capable of hydrolysing a glycolipid and a phospholipid, wherein said enzyme is incapable, or substantially incapable, of hydrolysing a triglyceride and/or a 1-monoglyceride.

In a fifteenth aspect, the present invention provides an edible oil, such as a soyabean or rapeseed oil, obtainable or obtained by the method according to the present invention.

In a sixteenth aspect, the present invention provides a protein which under dough conditions has one or more of the following characteristics:
i) is capable of hydrolysing a glycolipid and a phospholipid, wherein said enzyme is incapable, or substantially incapable, of hydrolysing a triglyceride and/or a 1-monoglyceride;
ii) a molecular weight of about 57 and/or about 87 kDa when determined by SDS-PAGE analysis;
wherein said protein is obtainable from *Vigna unguiculata*.

In a seventeenth aspect, the present invention provides a method of preparing a flour dough, said method comprising adding to the dough components an enzyme comprising the amino acid sequence shown in SEQ ID No. 12, or a variant, homologue or derivative thereof and mixing the dough components to obtain the dough.

For ease of reference, these and further aspects of the present invention are now discussed under appropriate section headings. However, the teachings under each section are not necessarily limited to each particular section.

PREFERABLE ASPECTS

Preferably the enzyme capable of hydrolysing a glycolipid and a phospholipid, wherein said enzyme is incapable, or substantially incapable, of hydrolysing a triglyceride and/or a 1-monoglyceride is a lipolytic acyl hyrolase (LAH) (E.C. 3.1.1.26).

Please note that the enzyme number E.C. 3.1.1.26 according to the International Union of Biochemistry and Molecular Biology (IUBMB) recommendations for Enzyme Nomenclature (1992) refers to a "galactolipase" which also acts on 2,3-di-O-acyl-1-O-(6-O-α-D-galactosyl-β-D-galactosyl)-D-glycerol, and phosphatidylcholine and other phospholipids. In the literature (such as, for example, Biochemica et Biophysica Acta 1215 (1994) 66–73) enzymes falling under the enzyme number E.C. 3.1.1.26 have been referred to as lipolytic acyl hydrolases (LAHs) and other such names. The terms galactolipase and lipolytic acyl hydrolase (LAH) as used herein are considered to be synonyms for the same enzyme, i.e. one falling under the E.C. classification 3.1.1.26 and having activity on both galactolipids and phospholipids.

Preferably the enzyme capable of hydrolysing a glycolipid and a phospholipid, wherein said enzyme is incapable, or substantially incapable, of hydrolysing a triglyceride and/or a 1-monoglyceride is isolated from soluble cowpea leaf extract and/or is isolated from wheat leaf thylakoids.

Suitably, the enzyme capable of hydrolysing a glycolipid and a phospholipid, wherein said enzyme is incapable, or substantially incapable, of hydrolysing a triglyceride and/or a 1-monoglyceride may have the amino acid sequence shown in SEQ ID No. 1 or may be a variant, homologue or derivative thereof.

Suitably, the enzyme capable of hydrolysing a glycolipid and a phospholipid, wherein said enzyme is incapable, or substantially incapable, of hydrolysing a triglyceride and/or a 1-monoglyceride may have the amino acid sequence shown in SEQ ID No. 1 or may have an amino acid sequence which is at least 75%, more preferably at least 85%, more preferably at least 90% homologous to SEQ ID No. 1.

Suitably, the enzyme capable of hydrolysing a glycolipid and a phospholipid, wherein said enzyme is incapable, or substantially incapable, of hydrolysing a triglyceride and/or a 1-monoglyceride may be encoded by the nucleotide sequence shown in SEQ ID No. 2 or may be a variant, homologue or derivative thereof.

Suitably, the enzyme capable of hydrolysing a glycolipid and a phospholipid, wherein said enzyme is incapable, or substantially incapable, of hydrolysing a triglyceride and/or a 1-monoglyceride may be encoded by the nucleotide sequence shown in SEQ ID No. 2 or may be encoded by a nucleotide sequence which is at least 75%, more preferably at least 85%, more preferably at least 90% homologous to SEQ ID No. 2.

Suitably, the enzyme capable of hydrolysing a glycolipid and a phospholipid, wherein said enzyme is incapable, or substantially incapable, of hydrolysing a triglyceride and/or a 1-monoglyceride may be a protein has a molecular weight of about 57 kDa and/or about 87 kDa when determined by SDS-PAGE analysis and which is obtainable from *Vigna unguiculata*.

Preferably, the protein having a molecular weight of about 57 and/or about 87 kDA is isolated using the same method as detailed herein.

The term "an enzyme that under dough conditions is capable of hydrolysing a glycolipid and a phospholipid, wherein said enzyme is incapable, or substantially incapable, or hydrolysing a triglyceride and/or a 1-monoglyceride includes an enzyme that under dough conditions hydrolyses a glycolipid and a phospholipid, but which does not, or does not substantially, hydrolyse a triglyceride and/or a 1-monoglyceride.

For some embodiments the enzyme may be added in the form of a composition comprising said enzyme.

An effective amount of the enzyme should be added, such that the enzyme, under dough conditions or degumming conditions, is capable of hydrolysing a glycolipid and a phospholipid, and is incapable, or substantially incapable, of hydrolysing a triglyceride and/or a 1-monoglyceride. Alternatively or in addition, an effective amount of a composition containing said enzyme may be added to the dough either directly to an already mixed dough or as a component of one or more dough components.

The term "effective amount" herein means an amount of the added enzyme which is sufficient to effect, under dough conditions or degumming conditions, detectable hydrolysis of one or more glycolipids and one or more phospholipids present in the dough, whilst the added enzyme does not affect, or does not significantly affect, triglyceride and/or 1-monoglyceride levels. More specifically, the term may relate to an amount of the added enzyme which does not only result in detectable hydrolysis of a glycolipid and phospholipid, whilst not substantially affecting the level of triglycerides and/or 1-monoglycerides, but which, in addition, results in the formation of enzymatic end products by hydrolysis of glycolipids and phospholipids, or the lack of formation of enzymatic end products by no, or substantially no, activity on triglycerides and/or 1-monoglycerides, at a level which results in improved properties of the dough or if the dough is baked, an improved quality of the baked product, such as enhanced bread volume, enhanced softness or improved crumb structure or the removal of polar lipids from an edible oil.

The terms "substantially incapable of hydrolysing a triglyceride and/or a 1-monoglyceride" and "having substantially no hydrolytic activity towards a triglyceride and/or a 1-monoglyceride" as used herein mean that the enzyme hydrolyses a triglyceride and/or a 1-monoglyceride only to an insignificant and/or undetectable degree.

Advantageously, at least one of the triglyceride, the 1-monoglyceride, the glycolipid and the phospholipid in the dough is a naturally occurring lipid component occurring in flour used for the dough.

Suitably, the phospholipid is phosphatidylcholine (PC) and/or the glycolipid is digalactosyldiglyceride (DGDG).

When it is the case that a polar lipid is added, suitably the polar lipid may be a phospholipid, such as one or more selected from the group consisting of phosphotidylinositol (PI), phosphatidylglycerol (PG), phosphatidylcholine (PC) and phosphatidylethanolamine (PE).

Preferably, the dough is a yeast leavened dough. Although, it is preferred to use the method of the present invention for the manufacture of yeast leavened bread products such as bread loaves, rolls or toast bread, the use of the method for any other type of dough and dough based products such as noodle and pasta products and cakes, the quality of which can be improved by the addition of the enzyme according to the present invention, is also contemplated.

Preferably, the enzyme is added in an amount which is in the range of 0.1 to 1000 units enzyme/kg flour. More preferably, the enzyme is added in an amount which is in the range of 1 to 100 units enzyme/kg flour.

Preferably, when the dough is a bread dough, the method comprises as a further step that the dough is baked to obtain a baked product. One particularly desired property of baked bread products is a high specific volume as defined in the examples. Accordingly, the addition of the enzyme of the invention preferably results in an increase of the specific volume of the baked product that is at least 10%, relative to a baked product made under identical conditions except that the enzyme is not added. More preferably, the increase of the specific volume is at least 20% such as at least 30%, e.g. at least 40%. Alternatively, the dough is a dough selected from the group consisting of a pasta dough, a noodle dough, and a cake dough or batter.

Preferably, the enzyme is added in an amount that results in an increase of the specific volume of the baked product that is at least 10%, relative to a baked product made under identical conditions except that the enzyme is not added.

The addition of the enzyme of the invention preferably results in an increase in the gluten index in the dough of at least 5%, relative to a dough without addition of the enzyme, the gluten index being determined by means of a Glutomatic 2200 apparatus.

The gluten index may be measured by means of a Glutomatic 2200 from Perten Instruments (Sweden) using the method detailed below: immediately after proofing, 15 g of dough should be scaled and placed in the Glutamatic 2200 and washed with 500 ml 2% NaCl solution for 10 min. The washed dough should then be transferred to a Gluten Index Centrifuge 2015 and the two gluten fractions should be scaled and the gluten index calculated according to the following equation:

Gluten Index=(weight of gluten remaining in the sieve×100)/total weight of gluten.

It has been found that the enzyme of the invention may be particularly active against certain glycolipids such as for example galactolipids including digalactodiglyceride (DGDG) which is converted into digalactomonoglyceride (DGMG) that is an effective surfactant. Preferably, at least 25% of the glycolipid initially present in the dough is hydrolysed and preferably at least 35% of the glycolipid is hydrolysed, more preferably at least 50%, at least 60% or at least 75% thereof.

Alternatively or in addition thereto, it has been found that the enzyme of the invention may be active against certain phospholipids which are converted into lysophospholipids. Preferably at least 25% of the phospholipid initially present in the dough is hydrolysed and preferably at least 35% of the phospholipid is hydrolysed, more preferably at least 50%, at least 60% or at least 75% thereof.

The activity of a lipase on triglyceride may depend on the pH of the substrate. Preferably, the enzyme has hydrolytic activity against a phospholipid and a glycolipid but no, or substantially no, hydrolytic activity against a triglyceride and/or a 1-monoglyceride in the pH range of 4.5–6.5.

Preferably, the enzyme as defined herein is incapable of hydrolysing a triglyceride and/or a 1-monoglyceride.

Preferably, the enzyme is incapable, or substantially incapable, of hydrolysing both a triglyceride and a 1-monoglyceride. Preferably the enzyme is incapable of hydrolysing both a triglyceride and a 1-monoglyceride. Alternatively, the enzyme may be capable of hydrolysing a triglyceride and a diglyceride, but be incapable, or substantially incapable, of hydrolysing a 1-monoglyceride. Suitably, the enzyme is incapable of hydrolysing a 1-monoglyceride.

It is known in the art that enzymes other than lipases may contribute to improved dough properties and quality of baked products. It is within the scope of the invention that, in addition to the enzyme of the invention, at least one further enzyme may be added to the dough or may be present in the dough improving composition. Such further enzymes include starch degrading enzymes such as endo- or exoamylases, pullulanases, starch degrading enzymes, debranching enzymes, hemicellulases including xylanases, cellulases, lipoxygenases and oxidoreductases, e.g. glucose oxidase, phospholipases and hexose oxidase.

Preferably, the further dough component in the composition, when one is present, is selected from the group consisting of cereal flour, yeast, a chemical leavening agent, a dough strengthening agent, an emulsifier, a sugar, an acylglycerol, a phospholipid, a glycolipid and a salt.

Suitably, the dough can be a fresh dough, optionally packed in a controlled atmosphere. The dough may be frozen.

Suitably, one or more enzymes according to the present invention may be added to the dough and/or be present in the dough improving composition and/or be added to the edible oil. Suitably, two or more, three or more, or four or more, enzymes according to the present invention may be added to the dough and/or be present in the dough improving composition and/or be added to the edible oil.

Preferably, the method of selecting enzymes according to the present invention may comprise screening the activity of enzymes on agar plates each containing either galactolipids, phospholipids, triglycerides or 1-monoglycerides as the substrate. Enzymes which are active towards phospholipids and glycolipids but which have no, or substantially no, activity towards triglycerides and/or 1-monoglycerides are selected.

Suitably, step (a) and/or (b) of the method of selecting an enzyme according to the present invention is carried out at a pH of 4.5–6.5.

Preferably, the enzyme tested by the method of selecting an enzyme according to the present invention is a lipase (E.C. 3.1.1.3) or a lipid acyl hydrolase (E.C. 3.1.1.26).

Preferably, in the method of preparing or developing an enzyme according to the present invention the insertion, deletion or substitution of at least one amino acid is in the lid region and/or near the active site and/or at the C-terminal of the amino acid sequence.

Preferably, the lid region is deleted.

Suitable enzymes may be prepared by modifying lipases (E.C. 3.1.1.3) and lipolytic acyl hydrolases (E.C. 3.1.1.26) to produce enzymes which are active towards phospholipids and glycolipids but which have no, or substantially no, activity towards triglycerides and/or 1-monoglycerides.

Suitable amino acid substitutions include substitutions of amino acids in or near the active site which change the hydrophilic properties around the active site. By way of example only, the amino acid substitutions may increase the number of polar amino acids in or near the active site.

Preferably, an enzyme is prepared in accordance with the present invention, which enzyme is capable of hydrolysing a glycolipid and a phospholipid and wherein said enzyme is incapable, or substantially incapable, of hydrolysing a triglyceride and/or a 1-monoglyceride in the pH range 4.5–6.5.

Suitably, the enzyme according to the present invention may have a greater activity towards glycolipids as compared with phospholipids. Suitably, the ratio of the % of hydrolysis of the initial glycolipids (i.e. DGDG) in the dough: the % hydrolysis of the initial phospholipids (i.e. phophatidylcholin) in the dough may be more than 10:1, for example, such as more than 15:1, more than 20:1, more than 30:1, or more than 40:1.

Alternatively, the enzyme according to the present invention may have a greater activity towards phospholipids as compared with glycolipids. For example, the ratio of the % of hydrolysis of the initial glycolipids (i.e. DGDG) in the dough: the % hydrolysis of the initial phospholipids (i.e. phophatidylcholin) in the dough may be more than 1:3, such as more than 1:5, more than 1:8, more than 1:10 or more than 1:15 for example.

Most cereal flours contain nonpolar lipids including triglycerides and polar lipids including phospholipids and glycolipids. The polar lipids can serve as substrates for the enzyme of the invention. Accordingly, in one embodiment of the method, at least one of the glycolipids, such as a galactolipid, including digalactosyldiglyceride (DGDG), and one of the phospholipids, such as phosphatidylcholine (PC), is a naturally occurring (or endogenous) lipid component occurring in the flour used for the dough.

However, flour dough may not contain sufficient amounts of these lipid substrates for the enzyme of the invention. It is therefore within the scope of the invention to supplement the dough with at least one of a glycolipid and a phospholipid to provide sufficient substrates for the enzyme. It will be appreciated that the expression "sufficient substrate" implies that neither of these lipid substrates is limiting for obtaining a dough improving or baked product improving effect as described above.

In addition or alternatively thereto, a supplementary nonpolar lipid such as an acylglycerol may be added. In accordance with the invention a variety of such lipids can be used such as e.g. vegetable oils, vegetable fats, animal oils, animal fats, such as for example butterfat, and shortening. In this connection, a particularly useful lipid is an oil or a fat derived from cereals such as oat oil. Oat oil typically contains, in addition to triglycerides, 5–25% phospholipids and 5–12% glycolipids. Oat oil can be fractionated to yield fractions having a high content of polar lipids (E. G. Hammond in Lipid in Cereal Technology edited by P. J. Barnes, Academic Press).

It is thus one aspect of the method of the invention that one or more phospholipids can be added to the dough. In this connection, useful phospholipids include phosphatidylinositol (PI), phosphatidylglycerol (PG), phosphatidylcholine (PC), lecithin and phosphatidylethanolamine (PE).

At least one of the triglyceride, the 1-monoglyceride, the glycolipid and the phospholipid may be added to the dough.

Surprisingly it has been found that the addition of an enzyme capable of hydrolysing a glycolipid and a phospholipid, wherein said enzyme is incapable, or substantially incapable, of hydrolysing a triglyceride and/or a 1-monoglyceride together with a glycolipid, in particular digalactosyldiglyceride (DGDG), results in improved bread volume and/or crumb structure. The improvements observed with the enzyme plus the glycolipid are even greater than the improvements observed with the enzyme alone. Thus, suitably, an enzyme having the specific properties defined herein may be used in combination with a glycolipid.

Edible oils, such as vegetable oils, for example soyabean oil or rapeseed oil, typically comprise triglycerides with a lower amount of polar lipids, such as phospholipids and glycolipids. It is often desired to remove the polar lipids from the vegetable oil in order to provide a clear, high quality oil product. The process of removing the polar lipids is often referred to as degumming. Thus, in accordance with the fifteenth apsect of the present invention the edible oil, for example a vegetable oil, may be degummed by use of an enzyme according to the present invention. Degumming is the first step of the edible oil refining process that removes the polar lipids, such as phospholipids, from the crude oil. Normally degumming is done by water or a wet process. For example, the phosphatides are converted to water-soluble lyso-phosphatides by an enzymatic catalysed hydrolysis, the water soluble lyso-phosphatides are then separated from the oil by centrifugation. The residual phosphorous content in the enzymatic degummed oil can be as low as 2 ppm phosphorous.

Preferably, the edible oil according to the fourteenth and fifteenth aspects of the present invention is a vegetable oil.

ADVANTAGES OF THE PRESENT INVENTION

An advantage of the present invention is that the enzyme of the present invention, which is active against glycolipids and phospholipids, but which is incapable, or substantially incapable, of hydrolysing triglycerides and/or 1-monoglycerides, when used in a dough, produces polyunsaturated fatty acids, because the endogenous wheat glycolipids and phospholipids contain high levels (>70%) of linoleic acid (C18:2) and linolenic acid (C18:3). These fatty acids are substrates for lipoxygenase and contribute to increased gluten strength and a whiter crumb.

A further or alternative advantage of the present invention is that endogenous polar lipids can be modified without the production of excess fatty acids. Thus, the dough is prevented from becoming too stiff and/or resultant bread volume can be increased and/or the production of off-flavours can be reduced and/or the negative effects on yeast activity can be alleviated or overcome. A yet further or alternative advantage of the present invention is that shortening, oil or milk fat added to the dough is not hydrolysed.

DETAILED DESCRIPTION OF THE PRESENT INVENTION

Enzymes According to the Present Invention

The enzyme having the properties as defined herein may be derived from a variety of sources including plants, animals and microorganisms such as bacterial and fungal species including yeast species. The enzyme of the invention may be derived from an organism that naturally produces the enzyme or it may be produced recombinantly by transforming an appropriate host cell with a gene coding for the enzyme. The enzyme can be an enzyme that comprises in itself active sites for all of its enzyme activities, but it is also possible to construct hybrid enzymes having the enzyme activities as defined herein by synthesis or by using recombinant DNA technology.

Alternatively, an enzyme which does not, initially at least, have the specific properties as defined herein can be modified, for example by altering the amino acid sequence thereof, in order to provide an enzyme having the properties as defined herein and having the desired substrate specificity. It is known in the art to modify enzymes by random mutagenesis (U.S. Pat. No. 4,814,331, WO 93/01285 and WO 95/22615) and to modify lipolytic enzymes by site-specific mutagenesis (WO 97/04079) to obtain improved performance thereof. The generally used concept has been to insert, delete or substitute amino acids within the structural part of the amino acid chain of a lipolytic enzyme in question. A suitable enzyme for modification is one that can hydrolyse ester bonds. Such enzymes include, for example, lipases, such as triacylglycerol lipase (E.C. 3.1.1.3), lipoprotein lipase (E.C. 3.1.1.34), monoglyceride lipase (E.C. 3.1.1.23), lysophospholipase, ferulic acid esterase and esterase (E.C. 3.1.1.1, E.C. 3.1.1.2) and lipolytic acyl hydrolases (E.C. 3.1.1.26) and phosphatidylinositol deacylase (E.C. 3.1.1.52).

Suitable enzymes for modification may be derived from a variety of sources including plants, animals and microorganisms, such as bacterial and fungal species including yeast species. Examples of suitable enzymes for modification are the *Pseudomonas* lipases, for example from *P. cepacia* (U.S. Pat. No. 5,290,694), *P. glumae* (Frenken N et al (1992) Appl. Envir. Microbiol. 58 3787–3791), *P. pseudoalcaligenes* (EP 0 334 462) or *Pseudomonas* sp. Strain SD 705 (WO95/06720, EP 0 721 981, WO 96/27002, EP 0 812 910). Alternatively, suitable enzymes for modification may be for example fungal lipolytic enzymes, such as lipolytic enzymes of the *Humicola* family and the *Zygomycetes* family and fungal cutinases. The *Humicola* family of lipolytic enzymes consists of the lipase from *H. lanuginosa* strain DSM 4109 and lipases having more than 50% homology with this lipase. The lipase from *H. lanuginosa* (synonym *Thermomyces lanuginosus*) is described in EP 0 258 068 and EP 0 305 216, and has the amino acid sequence shown in positions 1–269 of SEQ ID NO. 2 of U.S. Pat. No. 5,869,438.

Withers-Martinez et al (Structure 1996, 4:1363–1374) studied a guinea pig pancreatic lipase-related protein 2 (GPLRP2) which has activity on galactolipids and phospholipids and reduced activity on triglyceride. The crystal structure of this enzyme is shown and compared with a human pancreas lipase (HPL) with only activity on triglyceride and a chimeric mutant of lipase-related protein 2 (GPLRP2) consisting of the catalytic domain of GPLRP2 and the C-terminal domain of HPL (GPLRP2/HPL). The mutant GPLRP2/HPL has activity against phospholipids and galactolipids, but with further reduced activity on triglyceride as compared with the GPLRP2 enzyme. Also hornet venom (PLA1) was analyzed for comparison. Withers-Martinez et al (Structure 1996 Nov. 15; 4(11): 1363–74) studied the loops located above the active site of the guinea pig pancreatic lipase-related protein 2, human pancreatic lipase and a phospholipase A1 from hornet venom and found a relation between loop configuration and activity to triglyceride and phospholipids.

In GPLRP2 the lid domain is reduced in size compared to HPL, and only the β9 loop is conserved and therefore a less hydrophobic surface around the active site is observed. This may explain the reduced activity on triglyceride of GPLRP2 and GPLRP2/HPL compared to HPL.

Merely by way of example, a variant lipase with no activity on monoglyceride may be obtained by substitution of specific amino acids in or around the catalytic site of a lipase. For example the lipase from *Aspergillus tubingensis* which has the amino acid sequence as shown in SEQ ID No.

of each primer, 1xMutazyme reaction buffer and 200 µM dNTP mix in the Genemorph EP-PCR procedure. In Diversify EP-PCR procedure 1 ng DNA template, 2 U Titanium™ Taq DNA Polymerase, 10 µM of each primer, 3.5 mM $MgCl_2$, 480 µM $MnSO_4$ 200 µM dNTP mix and 40 µM dGTP were applied. Both EP-PCR procedures were executed in a total volume of 50 µL.

Primers designed for both EP-PCR procedures are shown in the table below. The primer JOM1 additionally introduces three A's (underscored) upstream of the start codon.

| Primer | Nucleotide sequence | $T_m$ [° C.] | Primer site [bp] | |
|---|---|---|---|---|
| JOM1 | 5'CAAGCTATACCAAGCATA CAATCAACTCCAAAATGTT CTCTGGACGGTTTG3' | 77.6 | 380–398 ($ADH_p$)→ 1–20 (LipA) | SEQ ID No. 5 |
| JOM2 | 5'CAAACCTCTGGCGAAGAA GTCCAAAGCTG3' | 69.3 | 400→428 (ADH3') | SEQ ID No. 6 |

3 and as taught in European Patent Publication No. 0 977 869, and which is encoded by the nucleotide sequence shown in SEQ ID No. 4, may be altered to provide such a variant lipase for use in accordance with the present invention.

The catalytic triad of SEQ ID No. 3 is Serine 173 (Ser173), Aspartic acid 228 (Asp228) and Histidine 285 (His285). Suitably, one or more of these amino acids of the catalytic triad may be substituted to change the hydrophilic properties of the catalytic triad.

One or more of the following amino acids in or around the catalytic site of SEQ ID No. 3 may be substituted to change the hydrophilic properties around the active site: Phe107–Phe123; Gly171–Gly175; Tyr198–Ile203; Thr224–Gly239; Ser270–Leu297.

For example, the procedure for mutating a "parent" lipase to provide a variant lipase with altered substrate activity in accordance with the present invention may include the following steps.

A. Expression Vector Construction

Figure 11:
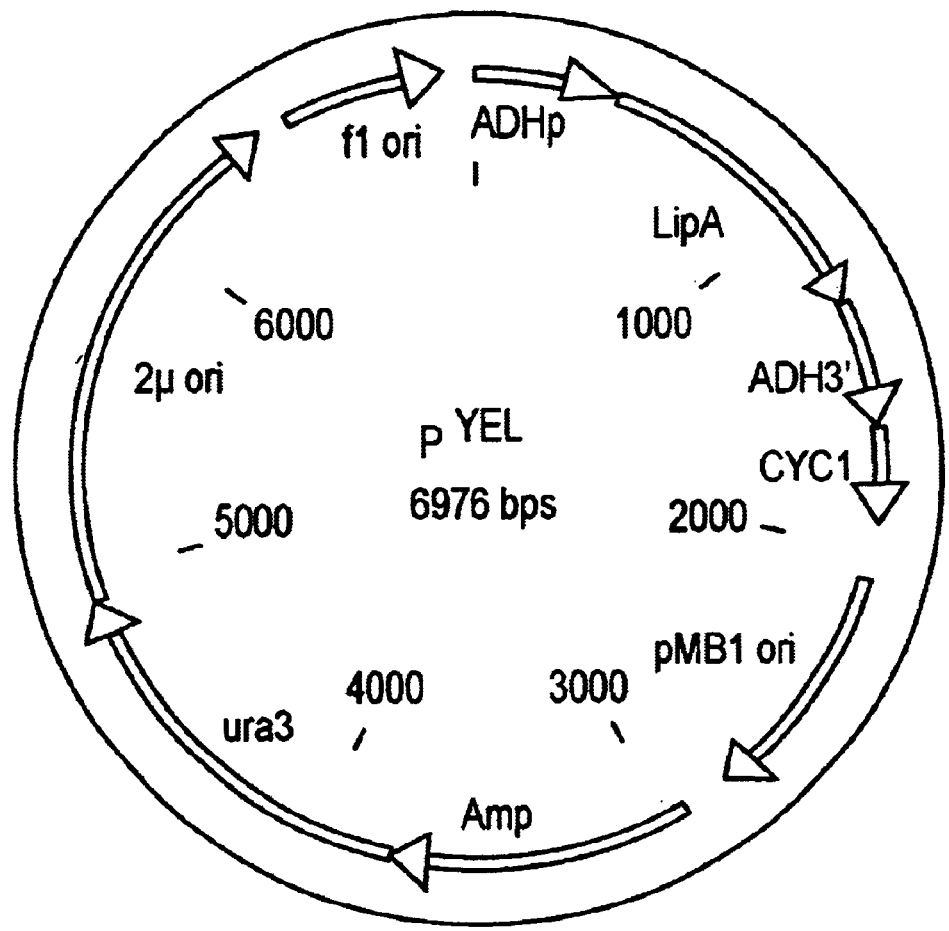

A vector, for example pYEL, may be constructed by replacing the inducible promoter, $Gal1_p$, with the constitutive promoter, $ADH_p$, and a lipase gene (for example the lipase gene from *Aspergillus tubigenisis* as taught in EP 0 977 869) may be incorporated by in vivo recombination in *S. cerevisiae*. FIG. 11 shows such an expression vector derived from pYES2

B. Random Mutagenesis by Error Prone PCR (EP-PCR)

Random mutagenesis libraries may then be created, for example, using two EP-PCR procedures; GeneMorph™ PCR Mutagenesis Kit and Diversify™ PCR Random Mutagenesis Kit, henceforward referred to as Genemorph and Diveresify, respectively.

Mutation frequency may be optimised in order to obtain 1–2 amino acid substitutions per lipase gene, for example per LipA gene. Optimisation of mutation frequency may be performed by varying initial amounts of template DNA (~0.65–40 ng) in Genemorph EP-PCR procedure and by varying concentrations of $MnSO_4$ (0–640 µM) and dGTP (40–120 µM) in Diversify EP-PCR procedure. The optimised EP-PCR procedures may contain contain: 0.65 ng DNA template, 2.5 U Mutazyme DNA Polymerase, 125 ng EP-PCR may be performed using a programmable thermal cycler with following conditions; GeneMorph™ PCR Mutagenesis Kit: 94° C. for 30 seconds, followed by 30 cycles of 94° C. for 30 seconds, 55° C. for 30 seconds and 72° C. for 2 minutes. Finally an additional extension of 10 minutes at 72° C. was applied. Diversify™ PCR Random Mutagenesis Kit: 94° C. for 30 seconds, followed by 25 cycles of 94° C. for 30 seconds and 68° C. for 1 minute.

C. Transformation and Expression

Transformed and competent cells may be prepared by a modification of the transformation procedure described in the pYES2 protocol (Catalog no. V825-20, Invitrogen, CA, USA), for example. A single colony of *Saccharomyces cerevisiae* CEN.PK113-5D may be inoculated in 20 mL YPD and grown overnight at 30° C. with shaking at 200 RPM. The overnight culture may be diluted with YPD to an $OD_{600}$ of 0.2–0.3 and incubated for an additional three hours at 30° C. and 200 RPM. Cells may be harvested by centrifugation at 4750 g and 20° C. for 5 minutes. The pellet may be washed by resuspension in 1 mL 1xTrisEDTA (1xTE), pH 8.0, and centrifuged for 5 minutes at 10000 g. Cells were made competent by adding 0.5 mL of 1xTE and 100 mM Lithium Acetate, pH 7.5.

Transformation may be performed by gently mixing 100 µg DNA with 50 µL competent *Saccharomyces cerevisiae* cells, 5 µL Yeastmaker Carrier DNA and 300 µL of 100 mM Lithium Acetate, 40% Polethylene glycol 3350 and 1xTE. The mixturemay be incubated at 30° C. with shaking at 1000 RPM for 30 minutes followed by incubation at 42° C. for 15 minutes. Afterwards cells may be transferred to ice and then pelleted at 11300 g for 5 seconds. The pellet may be resuspended in 1 mL YPD and incubated for 45 minutes at 30° C. and 200 RPM. A suspension volume of 150 µL was transferred to plates containing SC-ura and incubated for 3 days at 30° C. Transformation into competent *Saccharomyces cerevisiae* cells was furthermore utilised for cloning purposes using in vivo recombination, in which 100 ng of the lipase (for example LipA) or variants thereof may be co-transformed with 50 ng of BamHI linearised pYEA.

D. DNA Isolation

Plasmid DNA from *Escherichia coli* may be isolated by alkaline lysis using High Pure Plasmid Isolation Kit.

Plasmid DNA from *Saccharomyces cerevisiae* may be isolated as follows: cells may be pelleted by centrifugation at 1100 g for 15 minutes and re-suspended in 1 mL STET and 1.5 mL glass beads (425–600 microns). Additionally a volume of 1 mL STET was added and the mixture was incubated at 100° C. for 5 minutes. The solution may then be centrifuged for 15 minutes at 6500 g and supernatant may be transferred to an eppendorf tube, which was centrifuged for an additional 15 minutes at 27000 g. DNA may be extracted and purified from the supernatant using Qiagen-tip 20 from Plasmid Mini Purification Kit.

E. DNA Sequencing

Lipase (for example LipA) variants may be sequenced according to the dideoxy chain terminator procedure [Sanger et al., 1977]. Plasmid DNA for sequencing may be prepared using a modification of Plasmid Mini Purification Kit. Hereby a standard alkaline lysis may be performed instead of using Qiagen-tip 20 a. When using PCR amplified DNA for sequencing, DNA was isolated by Wizard® PCR Preps DNA purification System.

The sequencing reaction may be performed using ABI Prism® BigDye™ Terminators v3.0 Cycle Sequencing Kit (Danisco Biotechnology) or ABI Prism™ dRhodamine Terminator Cycle Sequencing Ready Reaction Kit (AAU) with DNA template and primer concentrations of 500 ng and 3.2 pmol, respectively. The sequencing reactions may be carried out using a programmable thermal cycler with following conditions: 25 cycles of 96° C. for 30 seconds, 50° C. for 15 seconds and 60° C. for 4 minutes. Purification of PCR products may be performed by ethanol precipitation and the pellet may be resuspended in 12 µL HIDI formamide (Danisco Biotechnology) or 12 µL template suppression reagent (AAU) and may be transferred to a Genetic Analyser sample tube with septa. Samples may be ran on an ABI Prism® 3100 Genetic Analyser (Danisco Biotechnology) or ABI Prism® 310 Genetic Analyser (AAU). Suitable primers for sequencing a variant LipA are presented in the table below. These primers anneal internally in Lip A.

| Primer | Nucleotide sequence | Primer site [bp] | $T_m$ [° C.] |
|---|---|---|---|
| JOM3 | 5'GCTCGTGGTCGCCTTCCGGGG 3' (SEQ ID No. 7) | 306–326 (LipA) | 68.2 |
| JOM4 | 5'GCCGGTGCAGAGGTCGTCG 3' (SEQ ID No. 8) | 399–381 (LipA) | 58.1 |
| JOM5 | 5'CCTCGAATCGGAAACTATGCGC 3' (SEQ ID No. 9) | 601–622 (LipA) | 61.6 |
| JOM13 | 5'TGTCACGGCGTCGGATATCG 3' (SEQ ID No. 10) | 768–787 (LipA) | 78 |
| JOM14 | 5'CTCATCCAACGTGGAAGTCG 3' (SEQ ID No. 11) | 108–89 (LipA) | 77 |

F. Screening for Lipase (Suitably Lipase 3) Variants: Altered Substrate Specificity Variants displaying DGDG and phospholipase activity, but no triglyceride activity may be identified using, for example, a preliminary high throughput plate screen followed by a quantitative screen, in which the enhancement is verified and quantified.

G. Production and Purification of Improved Variants

A single colony of selected variants may be inoculated in 50 mL of SC-ura medium and incubated at 30° C. and 250 rpm for two days, after which 25 mL may be transferred to 500 mL YPD medium and incubated for additionally two days at 30° C. and 200 rpm. The lipase produced may be separated from the culture by centrifugation for 15 min. The supernatant may be stored at −18° C. until further use.

Hydrophobic Interaction Chromatography

A volume of 250 mL supernatant may be equilibrated with $(NH_4)_2SO_4$ to obtain a final concentration of 1.0 M $(NH_4)_2SO_4$. The suspension was injected onto a SOURCE15PHE column containing phenyl hydrophobic ligands coupled to a 15 µm monodispersed rigid polystyrene/divinylbenzene matrix. The column may be packed to a final bed volume of 5.1 mL. Elution may be performed with 20 mM NaAc buffer pH 5.5 and a linear decreasing gradient of 1.0 M–0 M $(NH_4)_2SO_4$ at a rate of 5 mL/min for 20 min.

Identification of fractions containing lipase (for example lipase 3) and variants thereof inaccordance with the present invention may be performed by applying 15 µL of each fraction into wells on a plate containing suitable substrates to screen for phopsholipase activity, galactolipase activity and triglyceride hyrolyses.

Desalting

Selected fractions may be desalted using PD-10 desalting columns containing a Sephadex G-25 matrix packed to a final bed volume of 8.3 mL. The column may be pre-equilibrated with 20 mM TEA buffer pH 7.3, after which a sample volume of 2.5 mL was applied. Elution may be performed by applying 3.5 mL of 20 mM TEA buffer pH 7.3.

Anion Exchange Chromatography

Selected fractions may be injected onto a SOURCE15Q column containing quaternary ammonium ligands coupled to a 15 µm monodispersed rigid polystyrene/divinylbenzene matrix. The column may be packed to a final bed volume of 5.1 mL. Elution may be performed with 20 mM TEA buffer pH 7.3 and a linear increasing gradient of 0 M–1.0 M NaCl at a rate of 2 mL/min for 20 min.

H. Characterisation of Improved Variants

SDS-PAGE/Native Gel

Proteins may be separated according to size by SDS-PAGE using 1×running buffer, a 12% separating gel and 4% stacking gel prepared according to Laemmli (1970).

Equivalent amounts of sample and SDS sample buffer, containing 2-mercaptoethanol, may be incubated at 95° C. for 5 min. As standard a low range molecular weight marker was employed containing 0.64 µg Phosphorylase b, 0.83 µg Bovine serum albumin, 1.47 µg Ovalbumin, 0.83 µg Carbonic anhydrase, 0.88 µg Soybean trypsin inhibitor and 1.21 µg α-lactalbumin. Protein bands were visualised using Coommasie® G250 Stain.

For Native PAGE: Proteins may be separated according to mobility by native PAGE, in which no SDS was applied.

Lipases with only activity against galactolipids and phospholipids have not previously been used for baking. These types of lipases are rarely mentioned in the literature. However, Matos A. R. et al (FEBS Lett 2001 Mar. 2; 491(3): 188–92) isolated a 43 KDa protein from drought-stressed cowpea which was expressed in a baculovirus system. This enzyme showed preferentially galactolipid acyl hydrolase activity and some phospholipid activity but no activity on triacylglycerol (triglyceride). The amino acid sequence of this enzyme is shown in SEQ ID No. 1 and the nucleotide sequence encoding this enzyme is shown in SEQ ID No. 2. These types of enzyme are different from normal lipases (EC. 3.1.1.3) and the term lipolytic acyl hydrolase (LAH) (E.C. 3.1.1.26) is usually applied to these enzymes, which enzymes have only been described in the plant kingdom. The galactolipid acyl hydrolase described in Matos et al is suitable for use in accordance with the present invention.

The enzyme according to the present invention may be either a lipase (E.C. 3.1.1.3) or a lipolytic acyl hydrolase (E.C. 3.1.1.26), as long as it possesses the specified properties.

Sahsah et al (Biochem Biophys Acta 1994 Nov. 17;1215 (1–2):66–73) isolated a lipolytic acyl hydrolase from soluble cowpea leaf extract. The hydrolytic activity of this enzyme on different substrates showed the following relative activity digalactosyldiglyceride>monogalactosyldiglyceride>phosphatidylcholine>phosphatid ylglycerol. The enzyme had no activity on triacylglycerol (triglyceride). The enzyme taught in Sahsah et al is suitable for use in accordance with the present invention.

O'Sullivan et al (J. Plant Physiol. Vol. 131, pp 393–404 1987) disclosed a membrane-bound galactolipase associated with thylakoids of wheat leaves.

As the examples above illustrate lipases or lipolytic acyl hydrolases with activity on phospholipids and galactolipids alone, although apparently rare, exist in the nature and may be used in accordance with the present invention. In addition or alternatively other means of making a lipase with activity against phospholipids and galactolipids but no activity against triglycerides and/or 1-monoglycerides exist.

As mentioned above, Withers-Martinez (Structure 1996, 4:1363–1374) showed that a guinea pig lipase-related protein 2 (GPLRP 2) had activity on phospholipids and galactolipids and reduced activity on triglyceride. It is also indicated that the hydrophilicity around the active site can control the activity on triglyceride. This opens up the possibility of substitutions of amino acids in or near the active site which would further reduce the triglyceride activity by changing the hydrophilic properties around the active site.

It is well known that the activity of lipases can be altered by changing specific amino acids in the enzyme. Cordle et al (J. Lipid Res. 1998 September 39 (9): 1759–67) substituted tyrosine with the more polar aspartic acid and obtained a reduced activity on long chain fatty acids.

Carriere et al (Biochemistry 1997 Jan. 7 36(1): 239–48) removed the lid of a human pancreatic lipase in order to eliminate interfacial activation and found that its specific activity toward triglycerides was dramatically reduced. This article also reports that the C-terminal of a human pancreatic lipase is important for the interfacial stability.

A preferred lipase for baking with activity on phospholipids and galactolipids but with no activity on triglyceride can also be obtained by modifying the pH optimum for the triglyceride activity. Under normal conditions pH in a dough is in the range of 4.5–6.5. Ching T. Hou (Journal of Industrial Microbiology, 13 (1994) 242–248) screened a number of different lipases and found a number of lipases having triglyceride activity at pH 7.5 but no activity at pH 5.5.

By selecting a lipase with no activity at say pH 5.5 and modifying the area around the active site by site-directed or localized random mutagenesis to alter the hydrophilic properties of the surface around the active site and modifying the lid by site-directed or localised random mutagenesis, it is possible to obtain a lipase with activity on phospholipids and galactolipids and with the remaining triglyceride activity being active at a pH 7.5 or above, but with no activity at pH 6.5 or below, such as at pH 5.5.

Lipases can have different types of specificity (Inform Vol. 8, No. 6 640–650). The fatty acyl specificity of a lipase will have an impact on the type of fatty acid produced. Some lipases are very specific to unsaturated fatty acids, which in a dough system is preferable, as the polyunsaturated fatty acid is a substrate for endogenous or added lipoxygenase. Preferably, the enzyme according to the present invention preferentially hydrolyses unsaturated fatty acids. Suitably, in the method of preparing or developing an enzyme according to the present invention the insertion, deletion or substitution alters the fatty acyl specificity of the enzyme, such that the enzyme preferentially produces polyunsaturated fatty acids in the lipid moiety.

Suitable examples of enzymes having hydrolytic activity towards a phospholipid and a glycolipid and having no, or substantially no, hydrolytic activity towards a triglyceride and/or a 1-monoglyceride are presented in the section entitled Examples hereinbelow.

Cloning a Nucleotide Sequence Encoding an Enzyme According to the Present Invention A nucleotide sequence encoding either an enzyme which has the specific properties as defined herein or an enzyme which is suitable for modification may be isolated from any cell or organism producing said enzyme. Various methods are well known within the art for the isolation of nucleotide sequences.

For example, a genomic DNA and/or cDNA library may be constructed using chromosomal DNA or messenger RNA from the organism producing the enzyme. If the amino acid sequence of the enzyme is known, labelled oligonucleotide probes may be synthesised and used to identify enzyme-encoding clones from the genomic library prepared from the organism. Alternatively, a labelled oligonucleotide probe containing sequences homologous to another known enzyme gene could be used to identify enzyme-encoding clones. In the latter case, hybridisation and washing conditions of lower stringency are used.

Alternatively, enzyme-encoding clones could be identified by inserting fragments of genomic DNA into an expression vector, such as a plasmid, transforming enzyme-negative bacteria with the resulting genomic DNA library, and then plating the transformed bacteria onto agar containing a substrate for enzyme (i.e. phospholipids or galactolipids), thereby allowing clones expressing the enzyme to be identified.

In a yet further alternative, the nucleotide sequence encoding the enzyme may be prepared synthetically by established standard methods, e.g. the phosphoroamidite method described by Beucage S. L. et al (1981) Tetrahedron Letters 22, p 1859–1869, or the method described by Matthes et al (1984) EMBO J. 3, p 801–805. In the phosphoroamidite method, oligonucleotides are synthesised, e.g. in an automatic DNA synthesiser, purified, annealed, ligated and cloned in appropriate vectors.

The nucleotide sequence may be of mixed genomic and synthetic origin, mixed synthetic and cDNA origin, or mixed genomic and CDNA origin, prepared by ligating fragments of synthetic, genomic or cDNA origin (as appropriate) in accordance with standard techniques. Each ligated fragment corresponds to various parts of the entire nucleotide sequence. The DNA sequence may also be prepared by polymerase chain reaction (PCR) using specific primers, for instance as described in U.S. Pat. No. 4,683,202 or in Saiki R K et al (Science (1988) 239, pp 487–491).

Nucleotide Sequences

The present invention also encompasses nucleotide sequences encoding enzymes having the specific properties as defined herein. The term "nucleotide sequence" as used herein refers to an oligonucleotide sequence or polynucleotide sequence, and variant, homologues, fragments and derivatives thereof (such as portions thereof). The nucleotide sequence may be of genomic or synthetic or recombinant origin, which may be double-stranded or single-stranded whether representing the sense or antisense strand.

The term "nucleotide sequence" in relation to the present invention includes genomic DNA, cDNA, synthetic DNA, and RNA. Preferably it means DNA, more preferably cDNA for the coding sequence of the present invention.

In a preferred embodiment, the nucleotide sequence per se encoding an enzyme having the specific properties as defined herein does not cover the native nucleotide sequence in its natural environment when it is linked to its naturally associated sequence(s) that is/are also in its/their natural environment. For ease of reference, we shall call this preferred embodiment the "non-native nucleotide sequence". In this regard, the term "native nucleotide sequence" means an entire nucleotide sequence that is in its native environment and when operatively linked to an entire promoter with which it is naturally associated, which promoter is also in its native environment. Thus, the enzyme of the present invention can be expressed by a nucleotide sequence in its native organism but wherein the nucleotide sequence is not under the control of the promoter with which it is naturally associated within that organism.

Preferably the enzyme is not a native enzyme. In this regard, the term "native enzyme" means an entire enzyme that is in its native environment and when it has been expressed by its native nucleotide sequence.

Typically, the nucleotide sequence encoding enzymes having the specific properties as defined herein is prepared using recombinant DNA techniques (i.e. recombinant DNA). However, in an alternative embodiment of the invention, the nucleotide sequence could be synthesised, in whole or in part, using chemical methods well known in the art (see Caruthers M H et al (1980) Nuc Acids Res Symp Ser 215–23 and Horn T et al (1980) Nuc Acids Res Symp Ser 225–232).

Amino Acid Sequences

The present invention also encompasses amino acid sequences of enzymes having the specific properties as defined herein.

As used herein, the term "amino acid sequence" is synonymous with the term "polypeptide" and/or the term "protein". In some instances, the term "amino acid sequence" is synonymous with the term "peptide". In some instances, the term "amino acid sequence" is synonymous with the term "enzyme".

The amino acid sequence may be prepared/isolated from a suitable source, or it may be made synthetically or it may be prepared by use of recombinant DNA techniques.

Suitably, the amino acid sequences may be obtained from the isolated enzymes taught herein by standard techniques.

One suitable method for determining amino acid sequences from isolated enzymes is as follows:

Purified enzyme may be freeze-dried and 100 $\mu$g of the freeze-dried material may be dissolved in 50 $\mu$l of a mixture of 8 M urea and 0.4 M ammonium hydrogen carbonate, pH 8.4. The dissolved protein may be denatured and reduced for 15 minutes at 500° C. following overlay with nitrogen and addition of 5 $\mu$l of 45 mM dithiothreitol. After cooling to room temperature, 5 $\mu$l of 100 mM iodoacetamide may be added for the cysteine residues to be derivatized for 15 minutes at room temperature in the dark under nitrogen.

135 $\mu$l of water and 5 $\mu$g of endoproteinase Lys-C in 5 H1 of water may be added to the above reaction mixture and the digestion may be carried out at 37° C. in nitrogen for 24 hours.

The resulting peptides may be separated by reverse phase HPLC on a VYDAC C18 column (0.46×15 cm; 10 ym; The Separation Group, California, USA) using solvent A: 0.1 t TFA in water and solvent B: 0.1 k TFA in acetonitrile. Selected peptides may be re-chromatographed on a Develosil C18 column using the same solvent system, prior to N-terminal sequencing. Sequencing may be done using an Applied Biosystems 476A sequencer using pulsed liquid fast cycles according to the manufacturer's instructions (Applied Biosystems, California, USA).

Variants/Homologues/Derivatives

The present invention also encompasses the use of variants, homologues and derivatives of any amino acid sequence of an enzyme having the specific properties defined herein or of any nucleotide sequence encoding such an enzyme. Here, the term "homologue" means an entity having a certain homology with the subject amino acid sequences and the subject nucleotide sequences. Here, the term "homology" can be equated with "identity".

The variant, homologue and derivative amino acid sequence and/or nucleotide sequence should provide and/or encode an enzyme which retains the functional activity and/or enhances the activity of the enzyme.

In the present context, an homologous sequence is taken to include an amino acid sequence which may be at least 75, 85 or 90% identical, preferably at least 95 or 98% identical to the subject sequence. Typically, the homologues will comprise the same active sites etc. as the subject amino acid sequence. Although homology can also be considered in terms of similarity (i.e. amino acid residues having similar chemical properties/functions), in the context of the present invention it is preferred to express homology in terms of sequence identity.

In the present context, an homologous sequence is taken to include a nucleotide sequence which may be at least 75, 85 or 90% identical, preferably at least 95 or 98% identical to a nucleotide sequence encoding an enzyme of the present invention (the subject sequence). Typically, the homologues will comprise the same sequences that code for the active sites etc. as the subject sequence. Although homology can also be considered in terms of similarity (i.e. amino acid residues having similar chemical properties/functions), in the context of the present invention it is preferred to express homology in terms of sequence identity.

Homology comparisons can be conducted by eye, or more usually, with the aid of readily available sequence comparison programs. These commercially available computer programs can calculate % homology between two or more sequences.

% homology may be calculated over contiguous sequences, i.e. one sequence is aligned with the other sequence and each amino acid in one sequence is directly compared with the corresponding amino acid in the other sequence, one residue at a time. This is called an "ungapped" alignment. Typically, such ungapped alignments are performed only over a relatively short number of residues.

Although this is a very simple and consistent method, it fails to take into consideration that, for example, in an otherwise identical pair of sequences, one insertion or deletion will cause the following amino acid residues to be put out of alignment, thus potentially resulting in a large reduction in % homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local homology.

However, these more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, it is preferred to use the default values when using such software for sequence comparisons. For example when using the GCG Wisconsin Bestfit package the default gap penalty for amino acid sequences is −12 for a gap and −4 for each extension.

Calculation of maximum % homology therefore firstly requires the production of an optimal alignment, taking into consideration gap penalties. A suitable computer program for carrying out such an alignment is the GCG Wisconsin Bestfit package (Devereux et al 1984 Nuc. Acids Research 12 p387). Examples of other software than can perform sequence comparisons include, but are not limited to, the BLAST package (see Ausubel et al 1999 Short Protocols in Molecular Biology, 4<sup>th</sup> Ed—Chapter 18), FASTA (Altschul et al 1990 J. Mol. Biol. 403–410) and the GENEWORKS suite of comparison tools. Both BLAST and FASTA are available for offline and online searching (see Ausubel et al 1999, pages 7–58 to 7–60). However, for some applications, it is preferred to use the GCG Bestfit program. A new tool, called BLAST 2 Sequences is also available for comparing protein and nucleotide sequence (see FEMS Microbiol Lett 1999 174(2): 247–50; FEMS Microbiol Lett 1999 177(1): 187–8 and tatiana@ncbi.nlm.nih.gov).

Although the final % homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table if supplied (see user manual for further details). For some applications, it is preferred to use the public default values for the GCG package, or in the case of other software, the default matrix, such as BLOSUM62.

Once the software has produced an optimal alignment, it is possible to calculate % homology, preferably % sequence identity. The software typically does this as part of the sequence comparison and generates a numerical result.

The sequences may also have deletions, insertions or substitutions of amino acid residues which produce a silent change and result in a functionally equivalent substance. Deliberate amino acid substitutions may be made on the basis of similarity in polarity, charge, solubility, hydrophobicity, hydrophilicity, and/or the amphipathic nature of the residues as long as the secondary binding activity of the substance is retained. For example, negatively charged amino acids include aspartic acid and glutamic acid; positively charged amino acids include lysine and arginine; and amino acids with uncharged polar head groups having similar hydrophilicity values include leucine, isoleucine, valine, glycine, alanine, asparagine, glutamine, serine, threonine, phenylalanine, and tyrosine.

Conservative substitutions may be made, for example according to the Table below. Amino acids in the same block in the second column and preferably in the same line in the third column may be substituted for each other:

| ALIPHATIC | Non-polar | G A P |
| | | I L V |
| | Polar-uncharged | C S T M |
| | | N Q |
| | Polar-charged | D E |
| | | K R |
| AROMATIC | | H F W Y |

The present invention also encompasses homologous substitution (substitution and replacement are both used herein to mean the interchange of an existing amino acid residue, with an alternative residue) that may occur i.e. like-for-like substitution such as basic for basic, acidic for acidic, polar for polar etc. Non-homologous substitution may also occur i.e. from one class of residue to another or alternatively involving the inclusion of unnatural amino acids such as ornithine (hereinafter referred to as Z), diaminobutyric acid ornithine (hereinafter referred to as B), norleucine ornithine (hereinafter referred to as O), pyriylalanine, thienylalanine, naphthylalanine and phenylglycine.

Replacements may also be made by unnatural amino acids include; alpha* and alpha-disubstituted* amino acids, N-alkyl amino acids*, lactic acid*, halide derivatives of natural amino acids such as trifluorotyrosine*, p-Cl-phenylalanine*, p-Br-phenylalanine*, p-I-phenylalanine*, L-allyl-glycine*, β-alanine*, L-α-amino butyric acid*, L-γ-amino butyric acid*, L-α-amino isobutyric acid*, L-ε-amino caproic acid<sup>#</sup>, 7-amino heptanoic acid*, L-methionine sulfone<sup>#</sup>*, L-norleucine*, L-norvaline*, p-nitro-L-phenylalanine*, L-hydroxyproline#, L-thioproline*, methyl derivatives of phenylalanine (Phe) such as 4-methyl-Phe*, pentamethyl-Phe*, L-Phe (4-amino)#, L-Tyr (methyl)*, L-Phe (4-isopropyl)*, L-Tic (1,2,3,4-tetrahydroisoquinoline-3-carboxyl acid)*, L-diaminopropionic acid<sup>#</sup> and L-Phe (4-benzyl)*. The notation * has been utilised for the purpose of the discussion above (relating to homologous or non-homologous substitution), to indicate the hydrophobic nature of the derivative whereas # has been utilised to indicate the hydrophilic nature of the derivative, #* indicates amphipathic characteristics.

Variant amino acid sequences may include suitable spacer groups that may be inserted between any two amino acid residues of the sequence including alkyl groups such as methyl, ethyl or propyl groups in addition to amino acid spacers such as glycine or β-alanine residues. A further form of variation, involves the presence of one or more amino acid residues in peptoid form, will be well understood by those skilled in the art. For the avoidance of doubt, "the peptoid form" is used to refer to variant amino acid residues wherein the α-carbon substituent group is on the residue's nitrogen atom rather than the α-carbon. Processes for preparing peptides in the peptoid form are known in the art, for example Simon R J et al., PNAS (1992) 89(20), 9367–9371 and Horwell DC, Trends Biotechnol. (1995) 13(4), 132–134.

Nucleotide sequences encoding an enzyme having the specific properties defined herein may include within them synthetic or modified nucleotides. A number of different types of modification to oligonucleotides are known in the art. These include methylphosphonate and phosphorothioate backbones and/or the addition of acridine or polylysine chains at the 3' and/or 5' ends of the molecule. For the purposes of the present invention, it is to be understood that the nucleotide sequences described herein may be modified by any method available in the art. Such modifications may be carried out in order to enhance the in vivo activity or life span of nucleotide sequences.

The present invention also encompasses the use of nucleotide sequences that are complementary to the sequences discussed herein, or any derivative, fragment or derivative thereof. If the sequence is complementary to a fragment thereof then that sequence can be used as a probe to identify similar coding sequences in other organisms etc.

Polynucleotides which are not 100% homologous to the sequences of the present invention but fall within the scope of the invention can be obtained in a number of ways. Other variants of the sequences described herein may be obtained for example by probing DNA libraries made from a range of individuals, for example individuals from different populations. In addition, other viral/bacterial, or cellular homologues particularly cellular homologues found in mammalian cells (e.g. rat, mouse, bovine and primate cells), may be obtained and such homologues and fragments thereof in general will be capable of selectively hybridising to the sequences shown in the sequence listing herein. Such sequences may be obtained by probing cDNA libraries made from or genomic DNA libraries from other animal species, and probing such libraries with probes comprising all or part of any one of the sequences in the attached sequence listings under conditions of medium to high stringency. Similar considerations apply to obtaining species homologues and allelic variants of the polypeptide or nucleotide sequences of the invention.

Variants and strain/species homologues may also be obtained using degenerate PCR which will use primers designed to target sequences within the variants and homologues encoding conserved amino acid sequences within the sequences of the present invention. Conserved sequences can be predicted, for example, by aligning the amino acid sequences from several variants/homologues. Sequence alignments can be performed using computer software known in the art. For example the GCG Wisconsin PileUp program is widely used.

The primers used in degenerate PCR will contain one or more degenerate positions and will be used at stringency conditions lower than those used for cloning sequences with single sequence primers against known sequences.

Alternatively, such polynucleotides may be obtained by site directed mutagenesis of characterised sequences. This may be useful where for example silent codon sequence changes are required to optimise codon preferences for a particular host cell in which the polynucleotide sequences are being expressed. Other sequence changes may be desired in order to introduce restriction enzyme recognition sites, or to alter the property or function of the polypeptides encoded by the polynucleotides.

Polynucleotides (nucleotide sequences) of the invention may be used to produce a primer, e.g. a PCR primer, a primer for an alternative amplification reaction, a probe e.g. labelled with a revealing label by conventional means using radioactive or non-radioactive labels, or the polynucleotides may be cloned into vectors. Such primers, probes and other fragments will be at least 15, preferably at least 20, for example at least 25, 30 or 40 nucleotides in length, and are also encompassed by the term polynucleotides of the invention as used herein.

Polynucleotides such as DNA polynucleotides and probes according to the invention may be produced recombinantly, synthetically, or by any means available to those of skill in the art. They may also be cloned by standard techniques.

In general, primers will be produced by synthetic means, involving a stepwise manufacture of the desired nucleic acid sequence one nucleotide at a time. Techniques for accomplishing this using automated techniques are readily available in the art.

Longer polynucleotides will generally be produced using recombinant means, for example using a PCR (polymerase chain reaction) cloning techniques. This will involve making a pair of primers (e.g. of about 15 to 30 nucleotides) flanking a region of the lipid targeting sequence which it is desired to clone, bringing the primers into contact with mRNA or cDNA obtained from an animal or human cell, performing a polymerase chain reaction under conditions which bring about amplification of the desired region, isolating the amplified fragment (e.g. by purifying the reaction mixture on an agarose gel) and recovering the amplified DNA. The primers may be designed to contain suitable restriction enzyme recognition sites so that the amplified DNA can be cloned into a suitable cloning vector.

Hybridisation

The present invention also encompasses sequences that are complementary to the sequences of the present invention or sequences that are capable of hybridising either to the sequences of the present invention or to sequences that are complementary thereto.

The term "hybridisation" as used herein shall include "the process by which a strand of nucleic acid joins with a complementary strand through base pairing" as well as the process of amplification as carried out in polymerase chain reaction (PCR) technologies.

The present invention also encompasses the use of nucleotide sequences that are capable of hybridising to the sequences that are complementary to the subject sequences discussed herein, or any derivative, fragment or derivative thereof.

The term "variant" also encompasses sequences that are complementary to sequences that are capable of hybridising to the nucleotide sequences discussed herein.

Hybridisation conditions are based on the melting temperature (Tm) of the nucleotide binding complex, as taught in Berger and Kimmel (1987, Guide to Molecular Cloning Techniques, Methods in Enzymology, Vol. 152, Academic Press, San Diego Calif.), and confer a defined "stringency" as explained below.

Maximum stringency typically occurs at about $Tm-5°$ C. ($5°$ C. below the Tm of the probe); high stringency at about $5°$ C. to $10°$ C. below Tm; intermediate stringency at about $10°$ C. to $20°$ C. below Tm; and low stringency at about $20°$ C. to $25°$ C. below Tm. As will be understood by those of skill in the art, a maximum stringency hybridisation can be used to identify or detect identical nucleotide sequences while an intermediate (or low) stringency hybridisation can be used to identify or detect similar or related polynucleotide sequences.

Preferably, the term "variant" encompasses sequences that are complementary to sequences that are capable of hybridising under high stringency conditions or intermediate stringency conditions to nucleotide sequences encoding enzymes having the specific properties as defined herein.

More preferably, the term "variant" encompasses sequences that are complementary to sequences that are capable of hybridising under high stringent conditions (e.g. $65°$ C. and 0.1×SSC {1×SSC=0.15 M NaCl, 0.015 M Na-citrate pH 7.0}) to nucleotide sequences encoding enzymes having the specific properties as defined herein.

The present invention also relates to nucleotide sequences that can hybridise to the nucleotide sequences discussed herein (including complementary sequences of those discussed herein).

The present invention also relates to nucleotide sequences that are complementary to sequences that can hybridise to the nucleotide sequences discussed herein (including complementary sequences of those discussed herein).

Also included within the scope of the present invention are polynucleotide sequences that are capable of hybridising to the nucleotide sequences discussed herein under conditions of intermediate to maximal stringency.

In a preferred aspect, the present invention covers nucleotide sequences that can hybridise to the nucleotide sequences discussed herein, or the complement thereof, under stringent conditions (e.g. 50° C. and 0.2×SSC).

In a more preferred aspect, the present invention covers nucleotide sequences that can hybridise to the nucleotide sequences discussed herein, or the complement thereof, under high stringent conditions (e.g. 65° C. and 0.1×SSC).

Site-directed Mutagensis

Once an enzyme-encoding nucleotide sequence and/or amino acid sequence of the enzyme has been isolated, it may be desirable to mutate the sequence in order to prepare an enzyme having the desired properties of the present invention or to enhance the natural properties of the enzyme.

Mutations may be introduced using synthetic oligonucleotides. These oligonucleotides contain nucleotide sequences flanking the desired mutation sites.

A suitable method is disclosed in Morinaga et al (Biotechnology (1984) 2, p646–649), wherein a single-stranded gap of DNA, the enzyme-encoding sequence, is created in a vector carrying the enzyme gene. The synthetic nucleotide, bearing the desired mutation, is then annealed to a homologous portion of the single-stranded DNA. The remaining gap is then filled in with DNA polymerase I (Klenow fragment) and the construct is ligated using T4 ligase. Other suitable methods include the mega prima mutagenesis method of Sarkar G & Sommer S. S. (1990 BioTechniquesI 8, 404–407) and the QuickChange method of Papworth et al (1985 Nucleic. Acids Res. 13: 8765–8785).

U.S. Pat. No. 4,760,025 discloses the introduction of oligonucleotides encoding multiple mutations by performing minor alterations of the cassette. However, an even greater variety of mutations can be introduced at any one time by the above mentioned Morinaga method, because a multitude of oligonucleotides, of various lengths, can be introduced.

Another method of introducing mutations into enzyme-encoding nucleotide sequences is described in Nelson and Long (Analytical Biochemistry (1989), 180, p 147–151). This method involves the 3-step generation of a PCR fragment containing the desired mutation introduced by using a chemically synthesised DNA strand as one of the primers in the PCR reactions. From the PCR-generated fragment, a DNA fragment carrying the mutation may be isolated by cleavage with restriction endonucleases and reinserted into an expression plasmid.

Furthermore, Sierks et al (Protein Eng (1989) 2, 621–625 and Protein Eng (1990) 3, 193–198) describes site-directed mutagenesis in *Aspergillus* glucoamylase.

Suitably, a nucleotide sequence encoding either a lipase (E.C. 3.1.1.3) or a lipolytic acyl hydrolase (E.C. 3.1.1.26) may be subjected to site-directed mutagenesis in the lid region and/or near the active site and/or at the C-terminal of the amino acid sequence.

Preferably, the nucleotide sequence encoding either a lipase (E.C. 3.1.1.3) or a lipolytic acyl hydrolase (E.C. 3.1.1.26) may be subjected to site-directed mutagenesis near the active site to alter the hydrophilic properties of the surface around the active site.

Random Mutagenesis

Error prone PCR can be performed, for example by using the Diversify™ PCR Random Mutagenesis Kit from CLONTECH.

Localised Random Mutagenesis

A mutagenic primer (oligonucleotide) may be synthesised which corresponds to the part of the DNA sequence to be mutagenised except for the nucleotide(s) corresponding to amino acid codon(s) to be mutagenised. The primer will, in the 5' and 3' end, contain nucleotides corresponding to the sequence surrounding the sequence to be mutagenised. In the codons to be mutagenised different percentages of the four different nucleotides will be present at each position, giving the possibility for codons for different amino acids in the selected positions.

Subsequently, the resulting mutagenic primer may be used in a PCR reaction with a suitable opposite primer. The resulting PCR fragment may be cloned, perhaps after some additional modification, into a suitable vector, containing the rest of the coding region of the gene of interest.

Suitably, a nucleotide sequence encoding either a lipase (E.C. 3.1.1.3) or a lipolytic acyl hydrolase (E.C. 3.1.1.26) may be subjected to localised random mutagenesis in the lid region and/or near the active site and/or at the C-terminal of the amino acid sequence.

Preferably, the nucleotide sequence encoding either a lipase (E.C. 3.1.1.3) or a lipolytic acyl hydrolase (E.C. 3.1.1.26) may be subjected to localised random mutagenesis near the active site to alter the hydrophilic properties of the surface around the active site.

Expression of Enzymes

A nucleotide sequence encoding an enzyme having the specific properties as defined herein can be incorporated into a recombinant replicable vector. The vector may be used to replicate and express the nucleotide sequence, in enzyme form, in and/or from a compatible host cell. Expression may be controlled using control sequences which include promoters/enhancers and other expression regulation signals. Prokaryotic promoters and promoters functional in eukaryotic cells may be used. Tissue specific or stimuli specific promoters may be used. Chimeric promoters may also be used comprising sequence elements from two or more different promoters described above.

The enzyme produced by a host recombinant cell by expression of the nucleotide sequence may be secreted or may be contained intracellularly depending on the sequence and/or the vector used. The coding sequences can be designed with signal sequences which direct secretion of the substance coding sequences through a particular prokaryotic or eukaryotic cell membrane.

Expression Vector

The term "expression vector" means a construct capable of in vivo or in vitro expression.

Preferably, the expression vector is incorporated in the genome of the organism. The term "incorporated" preferably covers stable incorporation into the genome.

Preferably, the vector of the present invention comprises a construct according to the present invention. Alternatively expressed, preferably a nucleotide sequence coding for an enzyme having the specific properties as defined herein is present in a vector and wherein the nucleotide sequence is operably linked to regulatory sequences such that the regulatory sequences are capable of providing the expression of the nucleotide sequence by a suitable host organism, i.e. the vector is an expression vector.

The vectors of the present invention may be transformed into a suitable host cell as described below to provide for expression of a polypeptide or enzyme having the specific properties as defined herein. Thus, in a further aspect the invention provides a process for preparing polypeptides for subsequent use according to the present invention which comprises cultivating a host cell transformed or transfected with an expression vector as described above under conditions to provide for expression by the vector of a coding sequence encoding the polypeptides, and recovering the expressed polypeptides.

The vectors may be for example, plasmid, virus or phage vectors provided with an origin of replication, optionally a promoter for the expression of the said polynucleotide and optionally a regulator of the promoter. The choice of vector will often depend on the host cell into which it is to be introduced.

The vectors may contain one or more selectable marker genes. The most suitable selection systems for industrial micro-organisms are those formed by the group of selection markers which do not require a mutation in the host organism. Suitable selection markers may be the dal genes from *B. subtilis* or *B. licheniformis*, or one which confers antibiotic resistance such as ampicillin, kanamycin, chloramphenicol or tetracyclin resistance. Alternative selection markers may be the *Aspergillus* selection markers such as amdS, argB, niaD and sC, or a marker giving rise to hygromycin resistance. Examples of other fungal selection markers are the genes for ATP synthetase, subunit 9 (oliC), orotidine-5'-phosphate-decarboxylase (pvrA), phleomycin and benomyl resistance (benA). Examples of non-fungal selection markers are the bacterial G418 resistance gene (this may also be used in yeast, but not in filamentous fungi), the ampicillin resistance gene (*E. coli*), the neomycin resistance gene (*Bacillus*) and the *E. coli* uidA gene, coding for β-glucuronidase (GUS). Further suitable selection markers include the dal genes from *B subtilis* or *B. licheniformis*. Alternatively, the selection may be accomplished by co-transformation (as described in WO91/17243).

Vectors may be used in vitro, for example for the production of RNA or used to transfect or transform a host cell. Thus, nucleotide sequences encoding enzymes having the specific properties as defined herein can be incorporated into a recombinant vector (typically a replicable vector), for example a cloning or expression vector. The vector may be used to replicate the nucleic acid in a compatible host cell. Thus in a further embodiment, the invention provides a method of making nucleotide sequences encoding enzymes having the specific properties as defined herein by introducing a nucleotide sequence encoding such an enzyme into a replicable vector, introducing the vector into a compatible host cell, and growing the host cell under conditions which bring about replication of the vector. The vector may be recovered from the host cell. Suitable host cells are described below in connection with expression vectors.

The procedures used to ligate a DNA construct of the invention encoding an enzyme which has the specific properties as defined herein, and the regulatory sequences, and to insert them into suitable vectors containing the information necessary for replication, are well known to persons skilled in the art (for instance see Sambrook et al Molecular Cloning: A laboratory Manual, $2^{nd}$ Ed. (1989)).

The vector may further comprise a nucleotide sequence enabling the vector to replicate in the host cell in question. Examples of such sequences are the origins of replication of plasmids pUC19, pACYC177, pUB110, pE194, pAMB1 and pIJ702.

Regulatory Sequences

In some applications, a nucleotide sequence encoding an enzyme having the specific properties as defined herein may be operably linked to a regulatory sequence which is capable of providing for the expression of the nucleotide sequence, such as by the chosen host cell. By way of example, the present invention covers a vector comprising the nucleotide sequence of the present invention operably linked to such a regulatory sequence, i.e. the vector is an expression vector.

The term "operably linked" refers to a juxtaposition wherein the components described are in a relationship permitting them to function in their intended manner. A regulatory sequence "operably linked" to a coding sequence is ligated in such a way that expression of the coding sequence is achieved under condition compatible with the control sequences.

The term "regulatory sequences" includes promoters and enhancers and other expression regulation signals.

The term "promoter" is used in the normal sense of the art, e.g. an RNA polymerase binding site.

Enhanced expression of the nucleotide sequence encoding the enzyme having the specific properties as defined herein may also be achieved by the selection of heterologous regulatory regions, e.g. promoter, secretion leader and terminator regions, which serve to increase expression and, if desired, secretion levels of the protein of interest from the chosen expression host and/or to provide for the inducible control of the expression of the enzyme having the specific properties as defined herein. In eukaryotes, polyadenylation sequences may be operably connected to the nucleotide sequence encoding the enzyme.

Preferably, the nucleotide sequence of the present invention may be operably linked to at least a promoter.

Aside from the promoter native to the gene encoding the nucleotide sequence encoding an enzyme having the specific properties as defined herein, other promoters may be used to direct expression of the enzyme. The promoter may be selected for its efficiency in directing the expression of the nucleotide sequence of the present invention in the desired expression host.

In another embodiment, a constitutive promoter may be selected to direct the expression of the desired nucleotide sequence. Such an expression construct may provide additional advantages since it circumvents the need to culture the expression hosts on a medium containing an inducing substrate.

Examples of strong constitutive and/or inducible promoters which are preferred for use in fungal expression hosts are those which are obtainable from the fungal genes for xylanase (xlnA), phytase, ATP-synthetase, subunit 9 (oliC), triose phosphate isomerase (tpi), alcohol dehydrogenase (AdhA), α-amylase (amy), amyloglucosidase (AG—from the glaA gene), acetamidase (amdS) and glyceraldehyde-3-phosphate dehydrogenase (gpd) promoters. Other examples of useful promoters for transcription in a fungal host are those derived from the gene encoding *A. oryzae* TAKA amylase, the TPI (triose phosphate isomerase) promoter from *S. cerevisiae* (Alber et al (1982) J. Mol. Appl. Genet. 1, p419–434), *Rhizomucor miehei* aspartic proteinase, *A. niger* neutral α-amylase, *A. niger* acid stable α-amylase, *A. niger* glucoamylase, *Rhizomucor miehei* lipase, *A. oryzae* alkaline protease, *A oryzae* triose phosphate isomerase or *A. nidulans* acetamidase.

Examples of strong yeast promoters are those obtainable from the genes for alcohol dehydrogenase, lactase, 3-phosphoglycerate kinase and triosephosphate isomerase.

Examples of strong bacterial promoters are the α-amylase and SP02 promoters as well as promoters from extracellular protease genes. Examples of other suitable promoters for directing the transcription of the nucleotide sequence especially in a bacterial host are the promoters of the lac operon of *E. coli*, the *Streptomyces coelicolor* agarase gene dagA promoters, the promoters of the *Bacillus licheniformis*

α-amylase gene (amyL), the promoters of the *Bacillus stearothermophilus* maltogenic amylase gene (amyM), the promoters of the *Bacillus amyloliquefaciens* α-amylase (amyQ), the promoters of the *Bacillus subtilis* xylA and xylB genes.

Hybrid promoters may also be used to improve inducible regulation of the expression construct.

The promoter can additionally include features to ensure or to increase expression in a suitable host. For example, the features can be conserved regions such as a Pribnow Box or a TATA box. The promoter may even contain other sequences to affect (such as to maintain, enhance, decrease) the levels of expression of the nucleotide sequence of the present invention. For example, suitable other sequences include the Sh1-intron or an ADH intron. Other sequences include inducible elements—such as temperature, chemical, light or stress inducible elements. Also, suitable elements to enhance transcription or translation may be present. An example of the latter element is the TMV 5' signal sequence (see Sleat 1987 Gene 217, 217–225 and Dawson 1993 Plant Mol. Biol. 23: 97).

Constructs

The term "construct"—which is synonymous with terms such as "conjugate", "cassette" and "hybrid"—includes a nucleotide sequence encoding an enzyme having the specific properties as defined herein for use according to the present invention directly or indirectly attached to a promoter. An example of an indirect attachment is the provision of a suitable spacer group such as an intron sequence, such as the Sh1-intron or the ADH intron, intermediate the promoter and the nucleotide sequence of the present invention. The same is true for the term "fused" in relation to the present invention which includes direct or indirect attachment. In some cases, the terms do not cover the natural combination of the nucleotide sequence coding for the protein ordinarily associated with the wild type gene promoter and when they are both in their natural environment.

The construct may even contain or express a marker which allows for the selection of the genetic construct in, for example, a bacterium, preferably of the genus *Bacillus*, such as *Bacillus subtilis*, or plants into which it has been transferred. Various markers exist which may be used, such as for example those encoding mannose-6-phosphate isomerase (especially for plants) or those markers that provide for antibiotic resistance—e.g. resistance to G418, hygromycin, bleomycin, kanamycin and gentamycin.

For some applications, preferably the construct comprises at least a nucleotide sequence encoding an enzyme having the specific properties as defined herein operably linked to a promoter.

Host Cells

The term "host cell"—in relation to the present invention includes any cell that comprises either a nucleotide sequence encoding an enzyme having the specific properties as defined herein or an expression vector as described above and which is used in the recombinant production of an enzyme having the specific properties as defined herein.

Thus, a further embodiment of the present invention provides host cells transformed or transfected with a nucleotide sequence that expresses an enzyme having the specific properties as defined herein. Preferably said nucleotide sequence is carried in a vector for the replication and expression of the nucleotide sequence. The cells will be chosen to be compatible with the said vector and may for example be prokaryotic (for example bacterial), fungal, yeast or plant cells.

The gram negative bacterium *E. coli* is widely used as a host for heterologous gene expression. However, large amounts of heterologous protein tend to accumulate inside the cell. Subsequent purification of the desired protein from the bulk of *E. coli* intracellular proteins can sometimes be difficult.

In contrast to *E. coli*, Gram positive bacteria from the genus *Bacillus*, such as *B. subtilis, B. licheniformis, B. lentus, B. brevis, B. stearothermophilus, B. alkalophilus, B. amyloliquefaciens, B. coagulans, B. circulans, B. lautus, B. megaterium, B. thuringiensis, Streptomyces lividans* or *S. murinus*, may be very suitable as heterologous hosts because of their capability to secrete proteins into the culture medium. Other bacteria that may be suitable as hosts are those from the genera *Pseudomonas*.

Depending on the nature of the nucleotide sequence encoding an enzyme having the specific properties as defined herein, and/or the desirability for further processing of the expressed protein, eukaryotic hosts such as yeasts or other fungi may be preferred. In general, yeast cells are preferred over fungal cells because they are easier to manipulate. However, some proteins are either poorly secreted from the yeast cell, or in some cases are not processed properly (e.g. hyperglycosylation in yeast). In these instances, a different fungal host organism should be selected.

Suitable yeast organisms may be selected from the species of *Kluyveromyces, Saccharomyces* or *Schizosaccharomyces*, e.g. *Saccharomyces cerevisiae*, or *Hansenula* (disclosed in UK Patent Application No. 9927801.2).

Suitable filamentous fungus may be for example a strain belonging to a species of *Aspergillus*, such as *Aspergillus oryzae* or *Aspergillus niger*, or a strain of *Fusarium oxysporium, Fusarium graminearum* (in the perfect state named *Gribberella zeae*, previously *Sphaeria zeae*, synonym with *Gibberella roseum* and *Gibberella roseum* f. sp. *Cerealis*), or *Fusarium sulphureum* (in the perfect state named *Gibberella puricaris*, synonym with *Fusarium trichothercioides, Fusarium bactridioides, Fusarium sambucium, Fusarium roseum* and *Fusarium roseum* var. *graminearum*), *Fusarium cerealis* (synonym with *Fusarium crokkwellnse*) or *Fusarium venenatum*.

By way of example, typical expression hosts may be selected from *Aspergillus niger, Aspergillus niger* var. *tubigensis, Aspergillus niger* var. *awamori, Aspergillus aculeatis, Aspergillus nidulans, Aspergillus oryzae, Trichoderma reesei, Bacillus subtilis, Bacillus licheniformis, Bacillus amyloliquefaciens, Kluyveromyces lactis, Saccharomyces cerevisiae* and *Hansenula polymorpha*.

The use of suitable host cells—such as yeast, fungal and plant host cells—may provide for post-translational modifications (e.g. myristoylation, glycosylation, truncation, lapidation and tyrosine, serine or threonine phosphorylation) as may be needed to confer optimal biological activity on recombinant expression products of the present invention.

The host cell may be a protease deficient or protease minus strain. This may for example be the protease deficient strain *Aspergillus oryzae* JaL 125 having the alkaline protease gene named "alp" deleted. This strain is described in WO97/35956.

Organism

The term "organism" in relation to the present invention includes any organism that could comprise a nucleotide sequence coding for an enzyme having the specific properties as defined herein and/or products obtained therefrom.

Suitable organisms may include a prokaryote, fungus, yeast or a plant.

The term "transgenic organism" in relation to the present invention includes any organism that comprises a nucleotide sequence coding for an enzyme having the specific properties as defined herein and/or the products obtained therefrom, and/or wherein a promoter can allow expression of the nucleotide sequence coding for an enzyme having the specific properties as defined herein within the organism. Preferably the nucleotide sequence is incorporated in the genome of the organism.

The term "transgenic organism" does not cover native nucleotide coding sequences in their natural environment when they are under the control of their native promoter which is also in its natural environment.

Therefore, the transgenic organism of the present invention includes an organism comprising any one of, or combinations of, a nucleotide sequence coding for an enzyme having the specific properties as defined herein, constructs as defined herein, vectors as defined herein, plasmids as defined herein, cells as defined herein, or the products thereof. For example the transgenic organism can also comprise a nucleotide sequence coding for an enzyme having the specific properties as defined herein under the control of a heterologous promoter.

Transformation of Host Cells/Organism

As indicated earlier, the host organism can be a prokaryotic or a eukaryotic organism. Examples of suitable prokaryotic hosts include *E. coli* and *Bacillus subtilis*. Teachings on the transformation of prokaryotic hosts is well documented in the art, for example see Sambrook et al (Molecular Cloning: A Laboratory Manual, 2nd edition, 1989, Cold Spring Harbor Laboratory Press) and Ausubel et al., Current Protocols in Molecular Biology (1995), John Wiley & Sons, Inc.

If a prokaryotic host is used then the nucleotide sequence may need to be suitably modified before transformation—such as by removal of introns.

In another embodiment the transgenic organism can be a yeast. In this regard, yeast have also been widely used as a vehicle for heterologous gene expression. The species *Saccharomyces cerevisiae* has a long history of industrial use, including its use for heterologous gene expression. Expression of heterologous genes in *Saccharomyces cerevisiae* has been reviewed by Goodey et al (1987, Yeast Biotechnology, D R Berry et al, eds, pp 401–429, Allen and Unwin, London) and by King et al (1989, Molecular and Cell Biology of Yeasts, E F Walton and G T Yarronton, eds, pp 107–133, Blackie, Glasgow).

For several reasons *Saccharomyces cerevisiae* is well suited for heterologous gene expression. First, it is non-pathogenic to humans and it is incapable of producing certain endotoxins. Second, it has a long history of safe use following centuries of commercial exploitation for various purposes. This has led to wide public acceptability. Third, the extensive commercial use and research devoted to the organism has resulted in a wealth of knowledge about the genetics and physiology as well as large-scale fermentation characteristics of *Saccharomyces cerevisiae*.

A review of the principles of heterologous gene expression in *Saccharomyces cerevisiae* and secretion of gene products is given by E Hinchcliffe E Kenny (1993, "Yeast as a vehicle for the expression of heterologous genes", Yeasts, Vol 5, Anthony H Rose and J Stuart Harrison, eds, $2^{nd}$ edition, Academic Press Ltd.).

Several types of yeast vectors are available, including integrative vectors, which require recombination with the host genome for their maintenance, and autonomously replicating plasmid vectors.

In order to prepare the transgenic *Saccharomyces*, expression constructs are prepared by inserting the nucleotide sequence of the present invention into a construct designed for expression in yeast. Several types of constructs used for heterologous expression have been developed. The constructs contain a promoter active in yeast fused to the nucleotide sequence of the present invention, usually a promoter of yeast origin, such as the GAL1 promoter, is used. Usually a signal sequence of yeast origin, such as the sequence encoding the SUC2 signal peptide, is used. A terminator active in yeast ends the expression system.

For the transformation of yeast several transformation protocols have been developed. For example, a transgenic Saccharomyces according to the present invention can be prepared by following the teachings of Hinnen et al (1978, Proceedings of the National Academy of Sciences of the USA 75, 1929); Beggs, J D (1978, Nature, London, 275, 104); and Ito, H et al (1983, J Bacteriology 153, 163–168).

The transformed yeast cells are selected using various selective markers. Among the markers used for transformation are a number of auxotrophic markers such as LEU2, HIS4 and TRP1, and dominant antibiotic resistance markers such as aminoglycoside antibiotic markers, eg G418.

Filamentous fungi cells may be transformed by a process involving protoplast formation and transformation of the protoplasts followed by regeneration of the cell wall in a manner known. The use of *Aspergillus* as a host microorganism is described in EP 0 238 023.

Another host organism is a plant. The basic principle in the construction of genetically modified plants is to insert genetic information in the plant genome so as to obtain a stable maintenance of the inserted genetic material. Several techniques exist for inserting the genetic information, the two main principles being direct introduction of the genetic information and introduction of the genetic information by use of a vector system. A review of the general techniques may be found in articles by Potrykus (Annu Rev Plant Physiol Plant Mol Biol [1991] 42:205–225) and Christou (Agro-Food-Industry Hi-Tech March/April 1994 17–27). Further teachings on plant transformation may be found in EP-A-0449375.

Host cells transformed with the nucleotide sequence may be cultured under conditions conducive to the production of the encoded enzyme and which facilitate recovery of the enzyme from the cells and/or culture medium.

The medium used to cultivate the cells may be any conventional medium suitable for growing the host cell in questions and obtaining expression of the enzyme. Suitable media are available from commercial suppliers or may be prepared according to published recipes (e.g. as described in catalogues of the American Type Culture Collection).

The protein produced by a recombinant cell may be displayed on the surface of the cell. If desired, and as will be understood by those of skill in the art, expression vectors containing coding sequences can be designed with signal sequences which direct secretion of the coding sequences through a particular prokaryotic or eukaryotic cell membrane. Other recombinant constructions may join the coding sequence to nucleotide sequence encoding a polypeptide domain which will facilitate purification of soluble proteins (Kroll D J et al (1993) DNA Cell Biol 12:441–53).

The enzyme may be secreted from the host cells and may conveniently be recovered from the culture medium by well-known procedures, including separating the cells from the medium by centrifugation or filtration, and precipitating proteinaceous components of the medium by means of a salt such as ammonium sulphate, followed by the use of chromatographic procedures such as ion exchange chromatography, affinity chromatography, or the like.

Secretion

Often, it is desirable for the enzyme to be secreted from the expression host into the culture medium from where the enzyme may be more easily recovered. According to the present invention, the secretion leader sequence may be selected on the basis of the desired expression host. Hybrid signal sequences may also be used with the context of the present invention.

Typical examples of heterologous secretion leader sequences are those originating from the fungal amyloglucosidase (AG) gene (glaA—both 18 and 24 amino acid versions e.g. from *Aspergillus*), the a-factor gene (yeasts e.g. *Saccharomyces, Kluyveromyces* and *Hansenula*) or the α-amylase gene (Bacillus).

Fusion Proteins

An enzyme having the specific properties as defined herein may be produced as a fusion protein, for example to aid in extraction and purification thereof. Examples of fusion protein partners include glutathione-S-transferase (GST), 6×His, GAL4 (DNA binding and/or transcriptional activation domains) and (β-galactosidase. It may also be convenient to include a proteolytic cleavage site between the fusion protein partner and the protein sequence of interest to allow removal of fusion protein sequences. Preferably the fusion protein will not hinder the activity of the protein sequence.

The fusion protein may comprise an antigen or an antigenic determinant fused to the enzyme. In this embodiment, the fusion protein may be a non-naturally occurring fusion protein comprising a substance which may act as an adjuvant in the sense of providing a gencralised stimulation of the immune system. The antigen or antigenic determinant may be attached to either the amino or carboxy terminus of the enzyme.

In another embodiment of the invention, the amino acid sequence of an enzyme having the specific properties as defined herein may be ligated to a heterologous sequence to encode a fusion protein.

EXAMPLES

Figure 2:
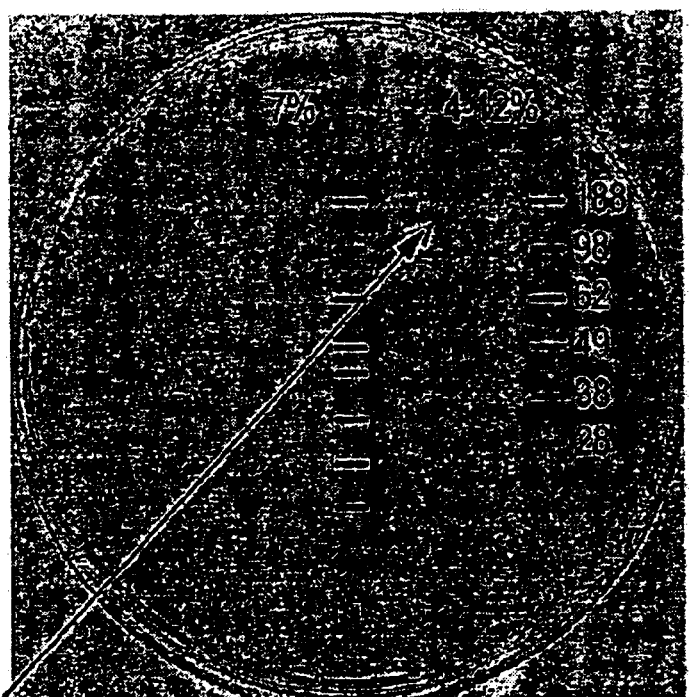
Figure 3:
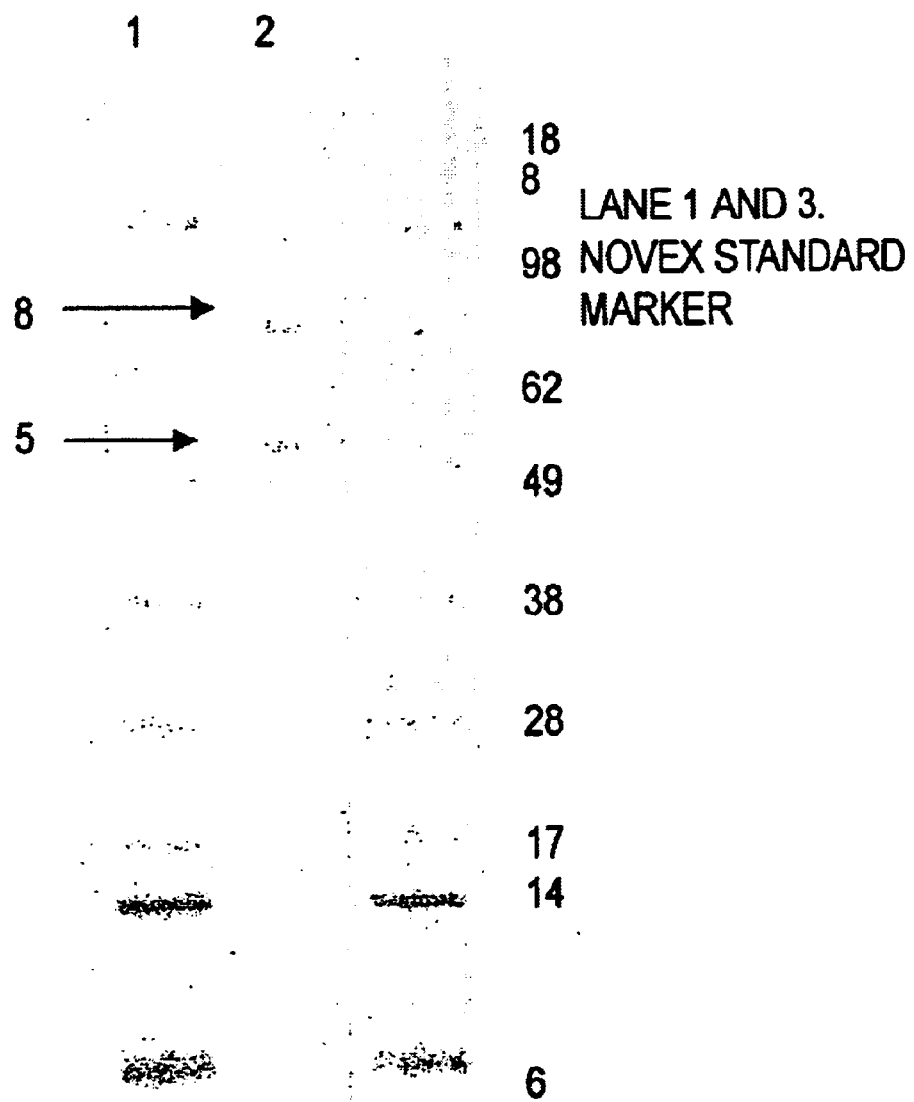
Figure 4:
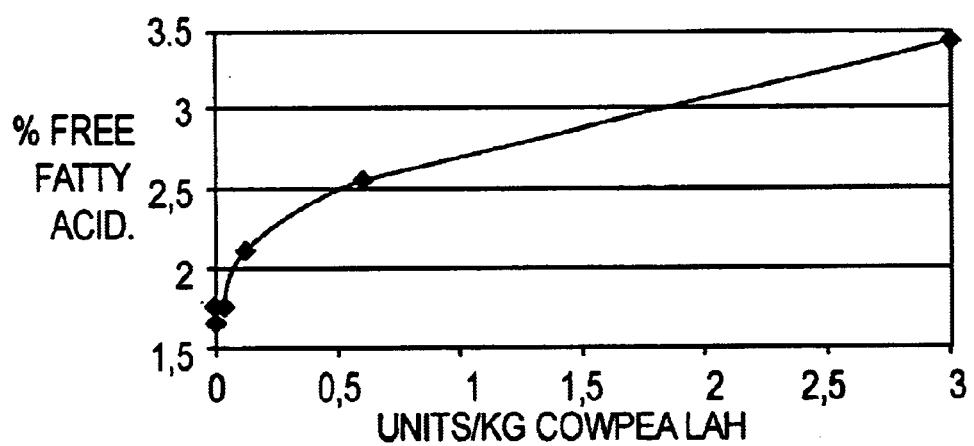
Figure 5:
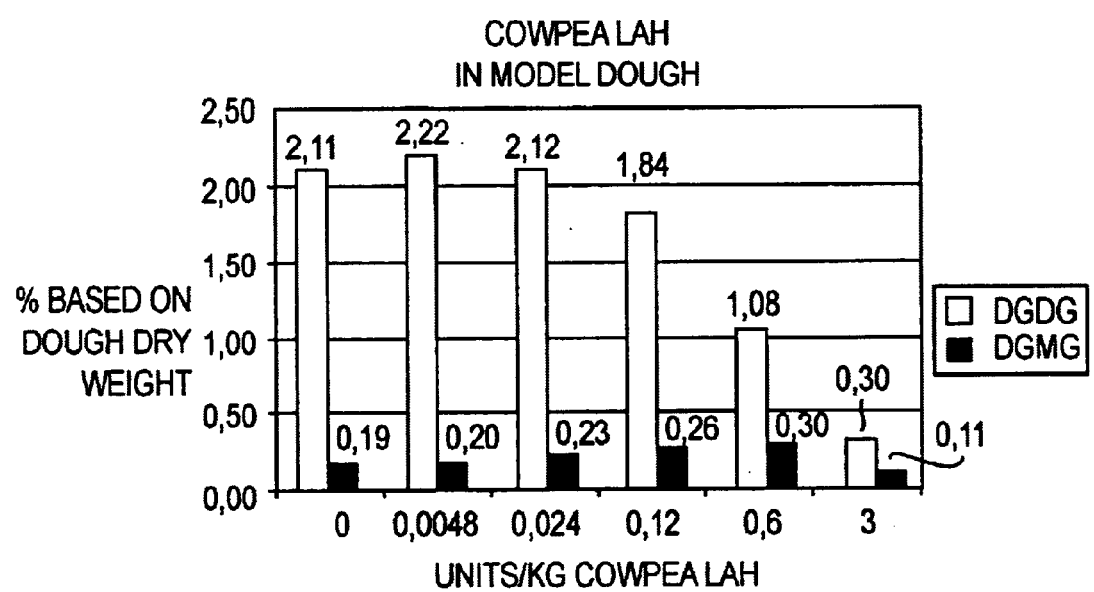
Figure 6:
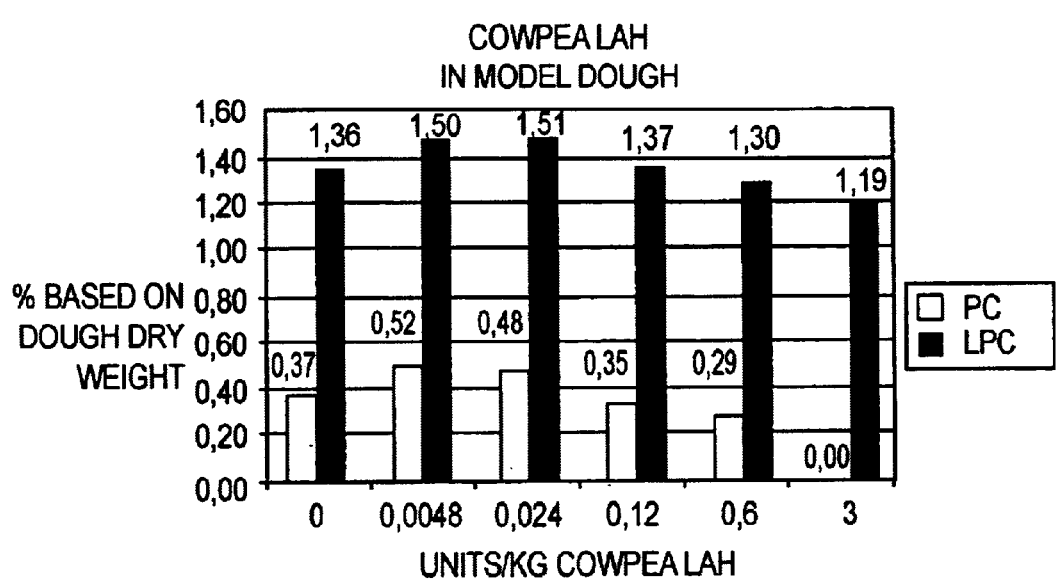
Figure 7:
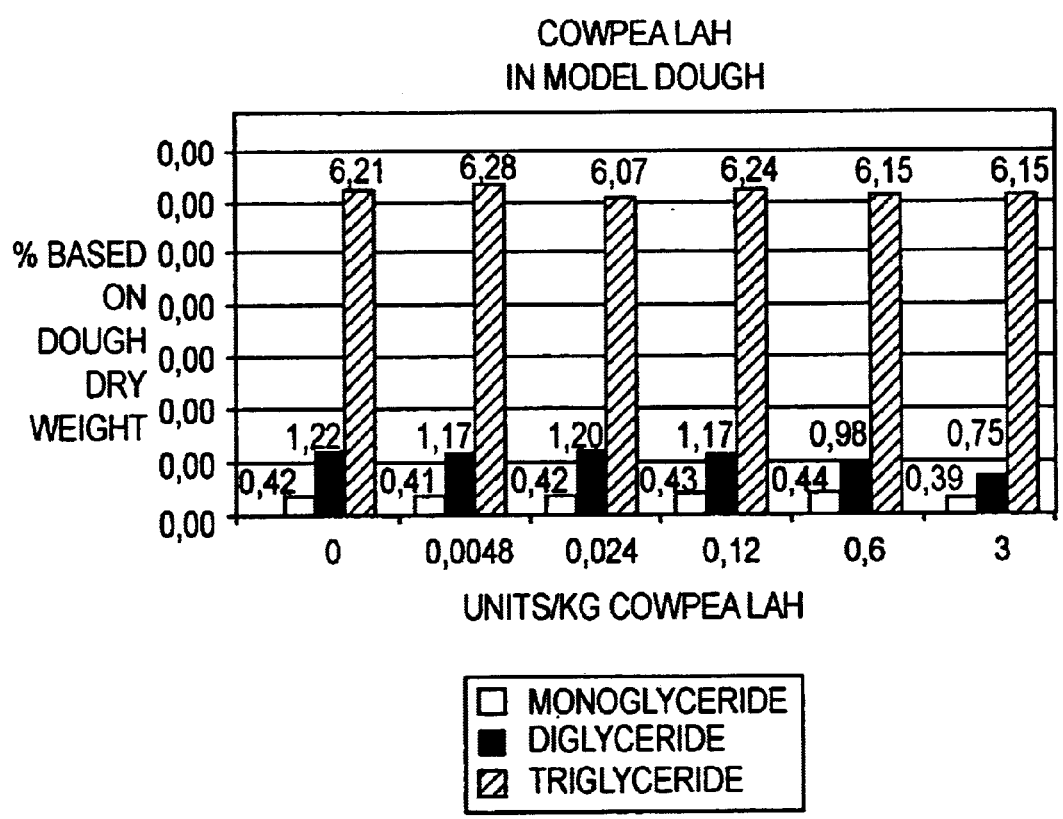
Figure 8:
Figure 9:
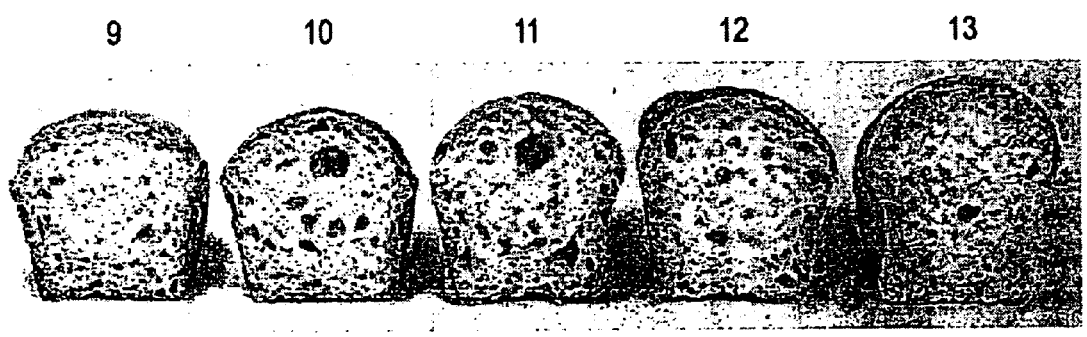
Figure 10:
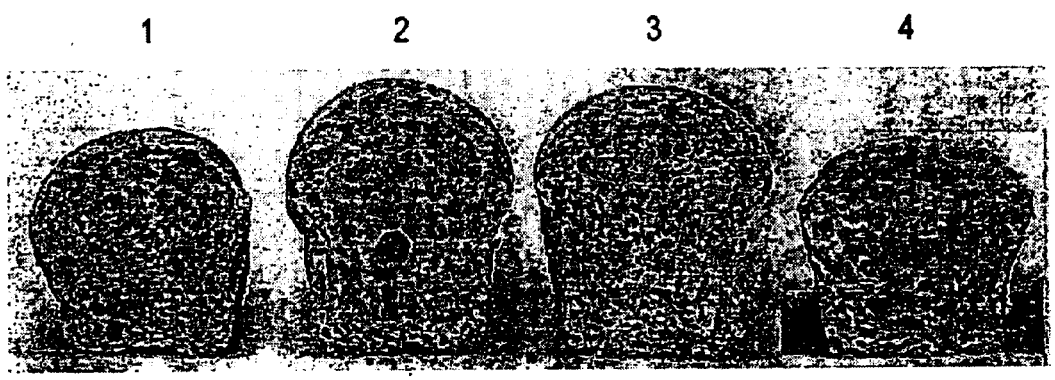
Figure 12:
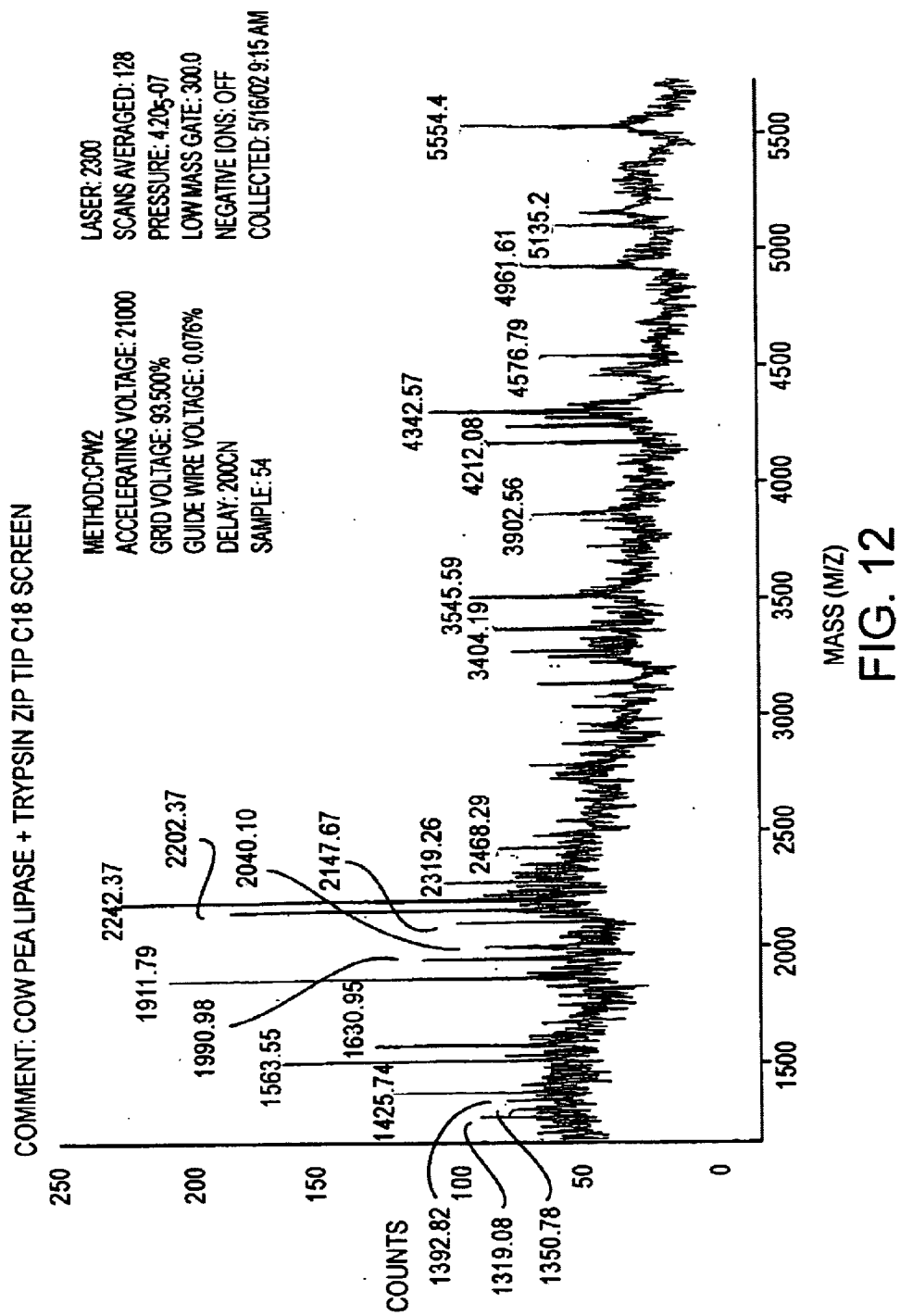

The present invention may now be described, by way of example only, in which reference may be made to the following figures:

FIG. 1, which shows a native-PAGE gel;

FIG. 2, which shows a galactolipid (DGDG) zymogram;

FIG. 3, which shows a SDS-PAGE gel;

FIG. 4, which shows a graph of the effect of cowpea LAH 1 in dough;

FIG. 5, which shows a graph of HPLC analysis of galactolipids in dough treated with cowpea LAH;

FIG. 6, which shows a graph of HPLC analysis of phospholipids in dough treated with cowpea LAH;

FIG. 7, which shows a graph of GLC analysis of non-polar lipids in dough treated with cowpea LAH;

FIG. 8, which shows a photograph of minibread wherein loaf 14 had 2% soy oil and loaf 15 had 2% soy oil+1.07 Units/kg of cowpea LAH added;

FIG. 9, which shows a photograph of minibread wherein loaf 9 is the control; loaf 10 had 1.07 Units/kg cowpea LAH added; loaf 11 had 1.07 Units/kg cowpea LAH+0.1% galactolipid added; loaf 12 had 1.07 Units/kg cowpea LAH+0.2% galactolipid added; and loaf 13 had 1.07 Units/kg cowpea LAH+0.4% galactolipid added;

FIG. 10, which shows a photograph of minibread wherein loaf 1 is the control; loaf 2 had 0.4% DGDG added; loaf 3 had 0.4% DGDG+0.4 Units/g Cowpea LAH added; and loaf 4 had 0.4 Units/g Cowpea LAH;

FIG. 11, which shows an expression vector which was derived from pYES2. The Gal1 promoter of pYES2 was removed and replaced by the constitutive ADH promoter. LipA was incorporated by in vivo recombination in *Saccharomyces cerevisiae*. Abbreviations: Amp, ampicillin resistant gene; ADH3', alcohol dehydrogenase 3' region; ADHP, alcohol dehydrogenase gene promoter; bps, base pairs; CYC1, Transcription terminator; f1 ori, f1 origin; Gal1p, galactose gene promoter; LipA, lipase gene from *Aspergillus tubigensis*; MCS, multiple cloning site; pMB1 ori, pUC derived origin, ura3, gene encoding uracil, $2\mu$ ori, $2\mu$origin;

FIG. 12, which shows a Maldi-TOF profile from the Lipolytic Acyl Hydrolase Enzyme from cowpea identified using the method detailed herein; and FIG. 13, which shows a peptide profile for VUPAT 1 (Matos et al FEBS Letters 491 (2001) 188–192).

MATERIALS AND METHODS

Enzymes:

Purified cowpea lipid acyl hydrolase (LAH)

Isolated membrane-bound galactolipase from wheat thylakoids

Flour:

Danish flour 'Sølvmel' nr. 2001084

Substrate:

Digalactosyldiglyceride, DGDG(55% pure) batch KGL01013, from Lipid Technologies Provider, Karlshamn, Sweden.

Procedures

Cowpea Lipolytic Acyl Hydrolase Enzyme (E.C. 3.1.1.26)

Plant Material

A lipolytic acyl hydrolase (LAH) capable of hydrolysing a glycolipid and a phospholipid, but incapable, or substantially incapable, of hydrolysing a triglyceride and/or a 1-monoglyceride, was isolated from cowpea. The lipolytic acyl hydrolases were obtained by a method based on that described in Sahsah et al (Biochemica et Biophysica Acta 1215 (1994) 66–73). An alternative suitable method may be that described in Matos et al (FEBS Letters 491 (2001) 188–192).

Cowpea beans were obtained from Morelos, Mexico. The plants were grown on Leca stones and watered with mineral nutrient solution according to Ellfolk, Biochim. Biophys. Acta 192 (1969) 486–493 (enriched with 6 mM of potassium nitrate), in a growth chamber, in pots of dimension 35×50 cm (approx. 50 plants in each pot), under temperature and light controlled conditions (16 hours daylight at 22° C. and 8 hours darkness at 18° C. with a relative air humidity of 72%). The leaves were harvested after 21 days of cultivation. At the harvest time the plants had 4–7 fully expanded mature leaves and 3–8 young leaves.

Extraction of Lipolytic Acyl Hydrolase Enzymes from Leaves 215 g of fresh leaves frozen in liquid nitrogen were homogenised in an industrial blender and extracted in 500 ml of 5 mM TRIS-buffer (pH 7.0), using an industrial blender (3 minutes mixing). The insoluble materials were removed by 20 minutes centrifugation at 15000 g. The resulting supernatant was finally filtered through a 0.45 µm filter (605 ml crude extract was collected).

Purification of the Lipolytic Acyl Hydrolase Enzymes

Step 1. Ultra Filtration

This step was carried out, using a 50 kDa Amicon ultra filtration unit. 122 ml concentrated crude extract was collected.

Step 2. Ammonium Sulphate Precipitation

Solid ammonium sulphate (68.5 g) was added to the crude extract to a final concentration of 80% saturation. The mixture was left stirring for 60 minutes at room temperature (25° C.). The precipitated protein was collected by centrifugation at 15000 g for 20 minutes. The precipitant was re-dissolved in 30 ml of 20 mM TEA buffer (pH 7.3). The insoluble material was removed by centrifugation at 15000 g for 20 minutes.

Step 3. Desalting (GFC)

The supernatant was desalted on a Sephadex G-25 column (5×25 cm, Pharmacia, Sweden), which was equilibrated with 20 mM TEA (pH 7.3) at a flow rate of 15 ml/min. The fractions containing galactolipase activity, (protein peak) were pooled (100 ml).

Step 4. Ion Exchange Chromatography (IEC)

The desalted sample was then applied to a Q-Sepharose Fast Flow (5×6 cm, Pharmacia, Sweden), equilibrated with 20 mM TEA (pH 7.3) at a flow rate 16 ml/minutes. To remove the unbound proteins, the column was washed with 250 ml of the same buffer, and bound proteins were eluted out by a linear gradient of 0–0.6 M NaCl in the same buffer. Fractions of 16 ml were collected and assayed for galactolipase activity. The fractions which contained galactolipase activity were pooled (128 ml).

Step 5. Ultrafiltration

This step was carried out as described in step 1.

A 16 ml desalted/concentrated sample was collected ($V_{max}$: 5.6 mOD/min. or 0.010 U/ml).

Baking trials were performed with a sample from this step.

Step 6. Ion Exchange Chromatography (IEC)

The desalted/concentrated (11 ml) sample was then applied to a Poros Q10 (0.5×5 cm, Applied Biosystem, USA), equilibrated with the same buffer as used in step 4, at a flow rate 1.5 ml/minute. Bound proteins were eluted by a linear gradient of 0–0.65 M NaCl in the same buffer. Fractions of 1.5 ml were collected and assayed for galactolipase activity. The fractions which contained galactolipase activity were pooled (6 ml).

Characterisation of Cowpea Lipolytic Acyl Hydrolase Enzyme

SDS-PAGE Analysis, Determination of Purity and Molecular Weight:

Purified lipolytic acyl hydrolase from IEC (step 6) was applied to a gel (NU-PAGE, 4–12%, MES-buffer, Novex, USA) and the gel was then coomassie stained. The gel revealed the existence of several bands (see FIG. 1). Attempts to further purify the lipolytic acyl hydrolase using several chromatographic techniques such as gel filtration chromatography, hydrophobic interaction chromatography, chromatofocusing, etc. did not improve the purity of the lipolytic acyl hydrolase.

Determination of Molecular Weight and Electro Elution of Lipolytic Acyl Hydrolase After Native PAGE:

Lipolytic Acyl Hydrolase was purified from cowpea (*Vigna unguiculata*) according to Sahsah et al. (Biochim. Biophys. Acta 1215 (1994) 66–73. Diffusion eluted lypolytic acyl hydrolase was then subjected to a SDS-PAGE gel. The gel was coomassie stained. This gel revealed 2 major bands at 57 and 84 kDa (see FIG. 3).

This preparation was subjected to trypsin digestion using the following protocol:

1. Add 50 µL 8M Urea in 0.4 M Ammonium bicarbonate buffer pH 8.1 (24.04 g urea, 1.581 g Ammonium bicarbonate per 50 mls)
2. Overlay with Nitrogen and incubate at 50° C. for 5 minutes.
3. Add 5 µL 50 mM DTT (8 mg/ml water)
4. Mix well, overlay with Nitrogen and incubate at 50° C. for 15 mintues.
5. Cool to room temperature.
6. Add 5 µL 100 mM Iodoacetamide (19 mg/ml water).
7. Mix well, overlay with Nitrogen and incubate in the dark at room temperature for 15 minutes.
8. Add 140 µL water, mix well and add trypsin at 1:25 (Trypsin is stored at 20° C. at 1 µg/µL in 0.1% TFA).
9. Overlay with Nitrogen and incubate overnight at 37° C.
10. Stop the reaction by freezing at −20° C.
11. Recover peptides by R.P. phase HPLC using a C18 column.

Post digestion peptide screening using ZipTip™ C18 desalting tips:

A. Wet the tip by aspirating in Methanol 4×10 µL.
B. Equilibrate the tip by washing 5×10 µL with 0.1% T.F.A. in water.
C. Bind peptides by aspirating 20× in the protein digest solution.
D. Remove salts by washing with 10×10 µL 0.1% T.F.A. in water.
E. Elute peptides directly on to a Maldi-TOF target plate with 2 µL of a 10 mg/ml α-cyano-4-hydroxycinnamic acid in 0.1% T.F.A. in 60% acetonitrile/water.
F. Ascertain the molecular weight of the peptides using a Voyage DE Maldi-TOF mass spectrometer.

The results of the Maldi-TOF analysis are presented in FIG. 12.

A comparison between the theoretical peptide profile (see FIG. 13) for VUPAT 1 (as taught in Matos et al. FEBS Letters 491 (2001) 188–192) and the experimentally obtained peptide profile for the lypolytic acyl hydrolase from cowpea obtained herein shows that the lipolytic acyl hydrolase purified herein is a different protein from that taught in Matos et al. This is also confirmed by the molecular weights determined by SDS-Page. In this study a molecular weight of 57 and 84 kDa is determined contrary to a molecular weight of 40 kDa reported by Sahsah et al.

A Membrane-Bound Lipolytic Acyl Hydrolase from Thylakoids from Wheat Leaves.

Plant Material

Wheat (Herward) was obtained from Pajbjergfonden, Odder, Denmark. Wheat grains were grown on paper at 25° C. and irrigated regularly. After one week the wheat leaves were harvested.

Homogenation Buffer:

50 mM HEPES, 350 mM Sorbitol, 1 mM EDTA, 1 mM $MgCl_2$, 1 mM $MnCl_2$ of 1 mM DTT, pH 8.3/NaOH). The buffer was kept on ice before use.

Extraction of Membrane-Bound Lipolytic Acyl Hydrolase 26 g wheat leaves were cut into small pieces (½ cm). 78 ml ice cold homogenation buffer was added. The leaves were homogenized in a high speed Ultra Turrax Mixer for 12 seconds.

Large particles were removed by filtration through 3 layers of Kleenex tissue. The filtrate was centrifuged at 250 g for 1 minute and the supernatant isolated.

The chloroplasts were isolated by centrifugation for 5 minutes at 1000 g. The pellets (comprising membrane-bound lipolytic acyl hydrolase) were resuspended in 1 ml homogenation buffer (microscopy analysis clearly showed the chloroplasts)

The pellets were used for testing in wheat model dough system.

Mini Baking Test

The following ingredients were added to a 50 g Brabrender mixing bowl and kneaded for 5 minutes at 30° C.: flour 50 g, dry yeast 1.0 g, sugar 0.8 g, salt 0.8 g, 70 ppm ascorbic acid and water (to a dough consistency of 400 Brabender units). Resting time was 10 min. at 34° C. The dough was scaled 15 g per dough. Then moulded on a special device where the dough was rolled between a wooden plate and a Plexiglas frame. The doughs were proofed in tins for 45 min. at 34° C., and baked in a Voss household oven for 8 min. 225° C.

After baking the breads were cooled to ambient temperature and after 20 min. The breads were scaled and the volume was determined by rape-seed displacement method.

The breads were also cut and crumb and crust evaluated.

Model Dough 10 g of flour and 0.020 g sodium chloride were mixed in a 10 g Farinograph mixing bowl for 1 minute either with or without enzymes. Subsequently water (500 Brabender units) was added and mixed for 5 minutes at 30° C. After mixing the dough was placed at 32° C. for 1 hour, and then frozen and freeze dried prior to further analysis.

Baking Tests (Danish Rolls)

Flour, Danish reform 1500 g, Compressed Yeast 90 g, sugar 24 g, salt 24 grams, water 400 Brabender units+2% were kneaded in a Hobart™ mixer with hook for 2 minutes low speed and 9 minutes high speed. The dough temperature was 26° C. The dough was scaled 1350 gram. Resting 10 min. at 30° C. and moulded on a Fortuna moulder. The dough was proofed 45 min. at 34° C. The dough was baked in a Bago-oven 18 min. 220° C. and steamed for 12 sec.

After cooling the rolls were scaled and the volume of the rolls was measured by the rape seed displacement method.

Specific bread volume $$\text{Specific volume} = \frac{\text{Volume of the bread, ml}}{\text{Weight of the bread, gram}}$$

The dough quality parameters were also evaluated.

| Dough elasticity | 1–10 |
|---|---|
| Stickiness | 1–10 |

Baking Tests (Toast Bread)

Flour, Danish reform 2000 g, Dry yeast 30 g, sugar 30 g, salt 30 gram and, water 400 Brabender units+3% was kneaded in a Hobart™ Mixer with hook for 2 min. at low speed and 10 min. at high speed. Dough temperature after mixing was 25° C. Resting time was 10 min. at 30° C. The dough was scaled 750 gram per dough. Then rested again for 5 min. at 33° C. and 85% RH. The dough was moulded on a Glimik moulder. The doughs were proofed in tins for 50 min. at 33° C., and baked in a Wachtel oven 40 min. 220° C. and steam injection for 16 sec.

After cooling the bread was scaled, and the volume of the bread was measured by the rape seed displacement method.

The crumb was also evaluated subjectively on a scale 1 to 10, where 1=course inhomogeneous and 10=nice homogeneous.

Three breads baked in tins with lids were stored at 20° C. and used for firmness measurements.

Firmness

Firmness of bread was measured on a Instron™ M model 4301 connected to a computer.

Conditions for measurement of bread firmness:

Load Cell Max. 100 N
Piston Diameter 50 mm
Cross Head Speed 200 mm/min
Compression 25%
Bread Slice thickness 11 mm The force is converted to $N/dm^2$.

The result was an average from measurement on 10 bread slices for every bread.

Lipid Extraction and Fatty Acid Analyses 10 g of fully proofed dough was immediately frozen and freeze dried. The freeze-dried dough was milled in a coffee mill and passed through an 800 micron screen. 1.5 g freeze-dried dough was scaled in a 15 ml centrifuge tube with screw top lid. 7.5 ml water saturated butanol (WSB) was added. The centrifuge tube was placed in a boiling water bath for 10 minutes. The tubes were placed in a Rotamix and rotated at 45 rpm for 20 minutes at ambient temperature and then placed in a boiling water bath again for a further 10 minutes prior to being Rotated on the Rotamix for a further 30 minutes at ambient temperature. The tubes were centrifuged at 3500 g for 5 minutes. 5 ml supernatant was transferred into a vial and the WSB was evaporated to dryness under a steam of nitrogen.

The free fatty acids in the extract were analysed as Cu-salts in isooctane measured at 715 nm and quantified according to a calibration curve based on oleic acid (Kwon D. Y. and Rhee J. S. (1986), A simple and rapid Colourimetric Method for Determination of Free Fatty Acids for Lipase Assay, JAOCS 63:89). Determination of Glycolipids and Phospholipids by HPLC.

1. Chromatographic Conditions

| System | Waters 600 | | | |
|---|---|---|---|---|
| Column | (LiChrospher ® 100 DIOL 5 µm) LiChroCART ® | LxD: 250 * 4.0 mm id. | | Temp: 50 ° C. |
| Injector | Waters 717plus Autosampler | | | Vol: 15 µl |
| Detector | Alltech 500 ELSD, evaporative light-scattering | | | Temp: 80° C. Gasflow: 1.50 L/min m/MFC |
| Integrator | Waters Millennium | | | |
| Mobile phase | A: 1000 Heptane/15 $CH_3COOH$ B: 500 Heptane/500 Isopropanol/15 $CH_3COOH$ C: 300 Heptane/600 Isopropanol/100 $H_2O$/15 $CH_3COOH$ | | | Flow: 1.25 ml/min Pressure: 1000–2500 psi |
| Gradient | Flow | Time(min) %A | %B | %C Comments |
| | 1.25 | 0 100 | 0 | 0 |
| | 1.25 | 10 60 | 40 | 0 |
| | 1.25 | 25 20 | 30 | 50 |
| | 1.25 | 35 0 | 0 | 100 |
| | 1.25 | 38 0 | 90 | 10 |
| | 1.25 | 40 30 | 70 | 0 |
| | 1.25 | 45 100 | 0 | 0 |
| | 1.25 | 55 100 | 0 | 0 new injection |

2. Stock Solution

ILPS* standard was dissolved in $CHCl_3/CH_3OH$ (75/25) ~2 mg/ml PC

Dilution of stock: 0.7, 0.14, 0.028,

| *Phosphatidic acid | PA | 5.13% |
|---|---|---|
| Phosphatidylethanolamine | PE | 12.74% |
| Phosphatidylcholine | PC | 14.76% |
| Phosphatidylinositol | PI | 10.13% |

*ILPS(International Lecithin and Phospholipid Society) standard is obtained from Spectral Service GmbH Köln, Germany.

3. Sample Preparation

Samples were dissolved in $CHCl_3/CH_3OH$ (75/25), sonicated and filtered through a 0.45 µm filter 4. Calibration Model
Calibration model: log-log linear calibration
The calibration curve for PC was used to calculate the amounts of the glycolipids and phospholipids.
Gas Chromatography
Perkin Elmer 8420 Capillary Gas Chromatography equipped with WCOT fused silica column 12.5 m×0.25 mm ID×0.1 µm 5%phenyl-methyl-silicone (CP Sil 8 CB from Crompack).
Carrier: Helium.
Injection: 1.5 µl with split.
Detector: FID. 385° C.

| Oven program: | 1 | 2 | 3 | 4 |
|---|---|---|---|---|
| Oven temperature, ° C. | 80 | 200 | 240 | 360 |
| Isothermal, time, min | 2 | 0 | 0 | 10 |
| Temperature rate, ° C./min | 20 | 10 | 12 | |

Sample preparation: 50 mg wheat lipid was dissolved in 12 ml heptane: pyridine 2:1 containing an internal standard heptadecane, 2 mg/ml. 500 µl of the sample was transferred to a crimp vial. 100 µl MSTFA (N-Methyl-N-trimethylsilyl-trifluoracetamid) was added and the reaction incubated for 15 minutes at 90° C. Calculation: Response factors for mono-di-triglycerides and free fatty acid were determined from reference mixtures of these components. Based on these response factors the mono-di-triglycerides and free fatty acids in wheat lipids were calculated.

Galactolipid (DGDG) Zymogram (Spot Plate) Assay.
Preparation of plates.
Solution 1.
2 g Agarose was dissolved in 110 ml water by heating to 90–100° C.
Solution 2.
1.2 g galactolipid was dispersed in 40 ml demineralised water. 50 ml 0.1M phosphate buffer pH 7 was added, subsequently 0.6 ml 0.2% Rhodamine B was also added.
Solution 1 was cooled to approx. 70° C. and solution 2 was added whilst stirring. 12 ml of the final mixture was transferred to a 7 cm Petri dish.
The plates were stored at 5° C. until use.
Assay.
Small holes of 1 mm in diameter was punched out of the gel and 10 µl enzyme solution was transferred to the hole. The formation of haloes in the agarose gels was followed as a function of time.
A blank without enzyme was also added to one of the holes for comparison.

Assay for Enzyme Activity
Preparation of substrate for enzymatic assay: The substrate, pNP-Caprate (C10), was dissolved in ethanol and diluted in 100 mM Na-Phosphate-buffer (pH 6.3) to a final concentration of 0.1 mg/ml substrate and 30% ethanol respectively, and kept at room temperature.
Assay method: The enzyme assay mixture contained 30 µl sample/blank and 250 µl substrate. The mixture was incubated at 35° C. for 30 minutes (420 nm) whilst simultaneously running an ELISA-reader (420 nm) kinetic program. The $V_{max}$ value was used for calculation of enzyme activity (U/ml). $V_{max}$ was converted to µmol from a standard curve for solutions of pNP measured under the same conditions as the sample. The enzyme activity is defined as the amount of enzyme which produce 1 µmol of pNP per min. at 35° C.

Screening Method for Random Mutagenesis
Libraries of enzymes obtained from random mutagenesis or localised random mutagenesis may be spread on cellulose acetate filters on agar plates containing growth media and incubated.

The cellulase acetate filters are then transferred to the selection plates and incubated at 37° C. for 2–6 hours. Cells harbouring active enzyme under the given conditions will develop clearing zones around the colonies. The positive variants can then be further purified and tested.

Results

Example 1

In the first series of dough experiments purified cowpea LAH was tested in 10 g dough in different concentrations in order to test the activity of the enzyme in dough and in order to find a suitable dosage for baking experiments. The activity of the enzyme was measured by analysing the level of free fatty acid in dough. The results are shown in Table 1 and FIG. 4.

TABLE 1

Effect of Cowpea LAH in Model Dough

| Cowpea LAH Units/kg flour | Fatty acid in dough ‰ |
|---|---|
| 3 | 3.44 |
| 0.6 | 2.55 |
| 0.12 | 2.13 |
| 0.024 | 1.78 |
| 0.0048 | 1.66 |
| 0 | 1.77 |

The results detailed in Table 1 and FIG. 4 clearly show that LAH from cowpea is active in dough during the production of free fatty acid.

Lipids extracted from the dough were further analysed by HPLC in order to study the effect on polar lipids in the dough.

Results from the HPLC analyses of dough lipids are shown in Table 2 and FIGS. 5 and 6.

TABLE 2

HPLC analysis of polar lipids in dough.

| Cowpea LAH Units/kg flour | ‰ DGDG | ‰ PC | ‰ DGMG | ‰ LPC |
|---|---|---|---|---|
| 0 | 2.11 | 0.37 | 0.19 | 1.36 |
| 0.0048 | 2.22 | 0.52 | 0.20 | 1.50 |
| 0.024 | 2.12 | 0.48 | 0.23 | 1.51 |
| 0.12 | 1.84 | 0.35 | 0.26 | 1.37 |
| 0.6 | 1.08 | 0.29 | 0.30 | 1.30 |
| 3.0 | 0.30 | 0.00 | 0.11 | 1.19 |

The non-polar lipids were analysed by GLC. The results from this analysis are shown in FIG. 7.

HPLC analysis clearly shows the effect of cowpea LAH on galactolipids, and at a high enzyme dosage digalactosyl-diglyceride (DGDG) is almost completely hydrolysed. The results also show a small increase in the concentration of the corresponding monoester, DGMG. At increased concentration of cowpea LAH, DGMG is however also hydrolysed. The same picture is also observed for phosphatidylcholine (PC) which is hydrolysed, followed by a small increase in the corresponding lysophosphatidylcholine. At increased concentration of cowpea LAH lysophosphatidylcholine is also hydrolysed in the dough.

In conclusion, it is observed that both galactolipids and phospholipids in dough are degraded by cowpea LAH.

The GLC analysis indicates no activity of cowpea LAH on triglyceride compared with the activity on polar lipids and the free fatty acid formation.

It is very clear that 3 Units/kg of cowpea LAH is a strong over dosage of this enzyme, which causes almost complete hydrolyses of all galactolipids in dough.

Example 2

Cowpea LAH was tested in minibread analysis in two different concentrations and compared to a control (without cowpea LAH added). The volume of the bread was evaluated as well as an evaluation of crumb structure and appearance. Fully proofed dough from this test was frozen and freeze dried and the dough lipid extracted. Isolated dough lipids were analysed by HPLC and GLC analysis.

The results from the baking test is shown in Table 3.

TABLE 3

Baking Test with Cowpea LAH

| Test no. | Cowpea LAH % in dough | Bread volume ml/g | Fatty acid in dough, ‰ |
|---|---|---|---|
| 1 | 0 | 3.09 | 2.63 |
| 2 | 0.05 | 3.11 | 2.75 |
| 3 | 0.15 | 3.3 | 2.96 |

Cowpea LAH clearly contributed to increased volume of the baked bread compared to the control, and the enzyme also contributed to improved crumb, with a more homogenous structure and a better appearance.

Results from lipid analysis of extracted lipids are shown in Table 4.

TABLE 4

GLC and HPLC Analyis of Dough Lipids

| Test no. | Monoglyceride ‰ | Diglyceride ‰ | Triglyceride ‰ | DGDG ‰ | DGMG ‰ |
|---|---|---|---|---|---|
| 1 | 0.43 | 0.99 | 4.94 | 2.09 | 0.22 |
| 2 | 0.43 | 0.95 | 4.98 | 2.03 | 0.27 |
| 3 | 0.43 | 0.96 | 5.11 | 1.92 | 0.28 |

The lipid analysis indicates that cowpea LAH does not hydrolyse the non-polar lipids. The level of triglyceride seem to increase a little, but this is within the experimental error. However, the enzyme clearly has an effect on the galactolipid in dough by degrading digalactolyldiglyceride (DGDG). An increase in the corresponding DGMG level is observed. The degree of hydrolysis of galactolipid is not very high, but sufficient to explain an improvement in baking quality of the enzyme.

Example 3

LAH isolated from cowpea was evaluated in baking tests as follows. The LAH was evaluated in hard crust rolls.

LAH was tested in a dosage of 0, 0.25, 0.5, 1 or 1.5 units enzyme/kg flour). Initial results show that the addition of 1.5 mg of LAH increased the loaf volume of the bread by more than 10% compared with bread with no enzyme and improved the dough handling properties.

Example 4

LAH was tested in bread according to the Danish toast bread procedure using Danish reform flour. LAH was tested at 0, 0.1, 0.25, 0.5, 1 or 1.5 units enzyme/kg flour. As references a dough was made without enzyme addition. After baking, the loaves were cooled and the loaf volume measured. Bread baked in tin with a lid were stored at ambient temperature and the crumb softness were evaluated after 1, 3 and 7 days storage at 22° C. wrapped in double plastic bags.

Initial results show that the addition of 1–1.5 units of LAH increases the loaf volume.

Initial results for firmness and elasticity show that LAH gives significantly softer crumb after 7 days storage compared with the control (without enzyme).

Preliminary results also show that LAH produces bread with a very good and homogeneous crumb structure.

Example 5

Cowpea LAH was tested in minibread in different concentrations according to Table 5.

TABLE 5

Baking test with cowpea LAH and fatty acid analysis of dough.

| Cowpea LAH Units/kg | Specific Bread volume, ml/g | Free fatty acid in dough, ‰ |
|---|---|---|
| 0 | 3.09 | 2.57 |
| 0.1195 | 3 | 2.72 |
| 0.239 | 3.2 | 2.81 |
| 0.478 | 3.15 | 3.07 |
| 0.956 | 3.15 | 3.28 |

Cowpea LAH clearly contributes to increased volume at low concentration (up to 0.239 Units/kg). At higher dosage there was no increase in volume but the crumb structure became more homogenous. Doughs from this experiment were extracted and the dough lipids isolated and analysed by HPLC and GLC as shown in Table 6.

TABLE 6

GLC and HPLC Analysis of Dough Lipids.

| Cowpea LAH % | Monoglyceride ‰ | Diglyceride ‰ | Triglyceride ‰ | DGDG ‰ | DGMG ‰ |
|---|---|---|---|---|---|
| 0 | 0.43 | 0.99 | 4.94 | 2.15 | 0.21 |
| 0.1195 | 0.40 | 0.96 | 5.04 | 2.08 | 0.23 |
| 0.239 | 0.41 | 1.23 | 5.21 | 2.01 | 0.20 |
| 0.478 | 0.43 | 0.90 | 5.09 | 1.89 | 0.24 |
| 0.956 | 0.41 | 1.01 | 5.23 | 1.60 | 0.20 |

The lipid analysis clearly confirms that cowpea LAH is not active on the nonpolar dough lipids (mono-di-and triglyceride), but the functionality is explained by the effect on polar lipids like digalactosyldiglyceride (DGDG), which are clearly hydrolysed. The results indicate some variations in level of di- and triglyceride, but the variations are random and not any indication of enzyme activity.

Example 6

Cowpea LAH was evaluated in minibread analysis. In this experiment the enzyme was tested alone and also in combination with a galactolipid isolated from oat. Results from the baking test and determination of free fatty acid are shown in Table 7.

TABLE 7

Cowpea LAH and Galactolipid(DGDG) in Minibread.

| Test no | DGDG, 55% pure % | Cowpea LAH Units/kg flour | Sp. Bread vol. Ml/g | Free fatty acid ‰ |
|---|---|---|---|---|
| 1 | 0 | 0 | 3 | 2.39 |
| 2 | 0.2 | 0 | 3.28 | 2.50 |
| 3 | 0 | 0.357 | 3.22 | 3.07 |
| 4 | 0.2 | 0.357 | 3.69 | 3.00 |

In this experiment it is shown that both cowpea LAH and galactolipid (55% DGDG) have a positive effect on the bread volume. Combining the two ingredients contribute to a clear synergistic effect as illustrated in Table 7. Both bread volume and crumb structure is significantly improved when cowpea LAH and DGDG are added.

Dough from this baking experiment was frozen and freeze dried and the dough lipid Extracted with water-saturated butanol. The isolated lipids were exposed to GLC and HPLC analyses. Results from these analyses are shown in Table 8.

TABLE 8

GLC and HPLC Analysis of Dough Lipids.

| Test no. | DGDG, 55% pure % | Cowpea LAH Units/kg flour | DGDG ‰ | DGMG ‰ | Triglyceride ‰ |
|---|---|---|---|---|---|
| 1 | 0 | 0 | 2.07 | 0.15 | 5.94 |
| 2 | 0.2 | 0 | 2.89 | 0.15 | 5.60 |
| 3 | 0 | 0.357 | 1.93 | 0.23 | not detected |
| 4 | 0.2 | 0.357 | 2.4 | 0.25 | 5.82 |

When galactolipids (test no 2) are added to the dough more galactolipids (DGDG) are also detected by HPLC analysis. Cowpea LAH has a strong hydrolysing effect on DGDG The hydrolysing effect is very clear both without DGDG added (test no. 3) and especially when DGDG is added (test no. 4). It is also observed that the level of the product of hydrolysis, namely DGMG, increases when cowpea LAH is added. As seen in the other experiments cowpea LAH has no hydrolysing effect on triglyceride.

Example 7

Cowpea LAH was evaluated in minibread analysis in combination with soy oil (Table 9).

TABLE 9

Cowpea LAH and Soy Oil in Minibread.

| Test no | Soy oil % | Cowpea LAH Units/kg flour | Sp. Bread vol. Ml/g | Free fatty acid ‰ |
|---|---|---|---|---|
| 14 | 2 | 0 | 3.3 | 2.00 |
| 15 | 2 | 1.07 | 3.3 | 3.35 |
| 16 | 2 | 2.14 | 3.12 | 3.75 |

In this experiment the cowpea LAH did not contribute to improvement in bread volume compared to bread baked with soy oil alone, but cowpea LAH clearly improved the crumb structure and appearance of the bread (FIG. 8).

Example 8

Cowpea LAH was evaluated in minibread analysis in combination with different concentrations of galactolipid (55%pure) (Table 10).

TABLE 10

Cowpea LAH and Galactolipid (55% Pure) in Minibread

| Test no | DGDG, 55% pure % | Cowpea LAH Units/kg flour | Sp. Bread vol. ml/g | Free fatty acid ‰ |
|---|---|---|---|---|
| 9 | 0 | 0 | 3.03 | 2.60 |
| 10 | 0 | 1.07 | 3.11 | 3.52 |
| 11 | 0.1 | 1.07 | 3.3 | 3.42 |
| 12 | 0.2 | 1.07 | 3.73 | 3.64 |
| 13 | 0.4 | 1.07 | 4.13 | 3.92 |

Table 10 shows that the addition of galactolipid in combination with 1.07 Units/kg galactolipid contributes to a strong improvement in both bread volume and crumb structure (FIG. 9).

Example 9

Purified LAH from cowpea was tested in minibread in combination with galactolipid DGDG.

The addition of ingredients to the dough is outlined in Table 11, as well as the bread volume of bread from these baking experiments.

TABLE 11

Baking test with cowpea LAH and galactolipid DGDG

| Test no | DGDG, 55% pure % | Cowpea LAH Units/kg flour | Sp. Bread volume ml/g |
|---|---|---|---|
| 1 | 0 | 0 | 2.92 |
| 2 | 0.4 | 0 | 4.11 |
| 3 | 0.4 | 0.71 | 4.36 |
| 4 | 0 | 0.71 | 3.14 |

It is clearly shown from the results in Table 11 that DGDG has a very positive effect on bread volume of the baked bread. Cowpea LAH also contributes to improved bread volume. The combination of Cowpea LAH and DGDG gave further improvement in bread volume and a better crumb structure was observed (FIG. 10).

Example 10

In this experiment isolated membrane bound LAH from wheat leaf chloroplasts were tested in a 10 gram model dough system. The dough was rested for 1 hour at 26° C. and then frozen and freeze dried.

The freeze dried dough was extracted with water saturated butanol (WSB) and the isolated dough lipids were exposed to GLC and HPLC analysis. The results from the lipid analysis are shown in Table 12.

TABLE 12

Effect of Membrane Bound LAH from Wheat Chloroplast in Dough. GLC Analysis of Lipids.

| Membrane-bound LAH % in dough | Free fatty acid ‰ | Mono-glyceride ‰ | Diglyceride ‰ | Tri-glyceride ‰ | DGDG ‰ |
|---|---|---|---|---|---|
| 0.1 | 3.06 | 0.32 | 0.84 | 4.20 | 0.82 |
| 0.5 | 4.40 | 0.30 | 0.57 | 3.80 | 0.00 |
| 1 | 4.83 | 0.30 | 0.51 | 3.96 | 0.00 |
| 2 | 5.70 | 0.27 | 0.37 | 4.12 | 0.00 |

The results in Table 12 confirm the lipolytic activity of the membrane-bound LAH enzyme from wheat chloroplasts in dough measured as a strong increase in free fatty acid in the dough. The results also have shown that the membrane-bound LAH enzyme from wheat chloroplasts has almost no effect on non-polar lipids, and the concentration of triglyceride is unchanged. The results also indicate a strong hydrolytic effect of the membrane bound LAH enzyme from wheat chloroplasts on the hydrolysis of galactolipids like digalactosyl diglyceride (DGDG), which is completely hydrolysed at higher dosages of the membrane-bound LAH enzyme.

Example 11

In this experiment an isolated LAH enzyme comprising the sequence shown in SEQ ID No. 12 was tested in a 10 gram model dough system. The dough was rested for 1 hour at 26° C. and then frozen and freeze dried.

Preliminary results show the enzyme comprising the sequence shown in SEQ ID No. 12 reduces the amounts of polar lipids in the oil whilst not significantly affecting the triglyceride levels of the oil.

Conclusion:

LAH enzymes from cowpea have been isolated and characterised and tested in model dough and minibaking experiments. This enzyme is active on the polar galactolipids and phospholipids in dough but no activity on triglycerides in dough was observed. A chloroplast bound LAH from wheat leaves has also been isolated and tested in model dough. This enzyme is also active against galactolipids and phospholipids in dough, but showed no activity on triglycerides.

Example 12

Vegetable oil, in particular rapeseed oil, was treated with LAH isolated from cowpea to effect degumming of the oil. The process used was essentially as per the enzyme-catalysed degumming process of vegetable oil generally taught in Buchold, H. (Fat Sci. Technol. 95 Jahrgang nr. 8, 1993, pp300-305), excepting that LAH was used.

Preliminary results show LAH to reduce the amounts of polar lipids in the oil whilst not significantly affecting the triglyceride levels of the oil.

All publications mentioned in the above specification are herein incorporated by reference. Various modifications and variations of the described methods and systems of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes of carrying out the invention which are obvious to those skilled in food chemistry/technology and biochemistry are intended to be within the scope of the following claims.

What is claimed is:

1. A method of preparing a flour dough, said method comprising adding to the dough components an enzyme that under dough conditions is capable of hydrolyzing a glycolipid and a phospholipid, wherein said enzyme is incapable, or substantially incapable, of hydrolyzing a triglyceride and/or a 1-monoglyceride, and mixing the dough components to obtain the dough.

2. A method according to claim 1 wherein the enzyme is incapable, or substantially incapable, of hydrolyzing both a triglyceride and a 1-monoglyceride.

3. A method according to claim 1 wherein the enzyme is capable of hydrolyzing a triglyceride and a diglyceride and wherein said enzyme is incapable, or substantially incapable, of hydrolyzing a 1-monoglyceride.

4. A method according to claim 1 wherein at least one of the triglyceride, the 1-monoglyceride, the glycolipid and the phospholipid is a naturally occurring lipid component occurring in flour used for the dough.

5. A method according to claim 1 wherein the phospholipid is phosphatidylcholine (PC).

6. A method according to claim 1 wherein the glycolipid is digalactosyldiglyceride (DGDG).

7. A method according to claim 1 wherein at least one of the triglyceride, the 1-monoglyceride, the glycolipid and the phospholipid is added to the dough.

8. A method according to claim 7 wherein the triglyceride is selected from the group consisting of a vegetable oil, a vegetable fat, an animal fat, shortening and milk fat.

9. A method according to claim 8 wherein the vegetable oil is a naturally occurring cereal oil.

10. A method according to claim 7 wherein the phospholipid is selected from the group consisting of phosphotidylinositol (PI), phosphatidylglycerol (PG), phosphatidylcholine (PC) and phosphatidylethanolamine (PE).

11. A method according to claim 1 wherein the dough is a yeast leavened dough.

12. A method according to claim 1 wherein the enzyme is added in an amount which is in the range of 0.1 to 1000 units enzyme/kg flour.

13. A method according to claim 12 wherein the enzyme is added in an amount which is in the range of 1 to 100 units enzyme/kg flour.

14. A method according to claim 1 wherein the dough is a bread dough, the method comprising as a further step that the dough is baked to obtain a baked product.

15. A method according to claim 1 wherein the dough is selected from the group consisting of a pasta dough, a noodle dough, a cake dough and a cake batter.

16. A method according to claim 1 wherein the enzyme is added in an amount that results in an increase of the specific volume of the baked product that is at least 10%, relative to a baked product made under identical conditions except that the enzyme is not added.

17. A method according to claim 1 wherein a further enzyme is added to the dough.

18. A method according to claim 17 wherein the further enzyme is selected from the group consisting of a lipase, a starch degrading enzyme, a hemicellulase, a cellulose, and an oxidoreductase.

19. A method according to claim 1 wherein at least 25% of the glycolipid initially present in the dough is hydrolysed.

20. A method according to claim 1 wherein at least 25% of the phospholipid initially present in the dough is hydrolysed.

21. A method according to claim 1 wherein the enzyme has hydrolytic activity against a phospholipid and a glycolipid but no, or substantially no, hydrolytic activity against a triglyceride and/or a 1-monoglyceride in the pH range of 4.5–6.5.

22. A dough improving composition comprising an enzyme that, under dough conditions, is capable of hydrolyzing a glycolipid and a phospholipids, wherein said enzyme is incapable, or substantially incapable, of hydrolyzing a triglyceride and/or a 1-monoglyceride, and one further dough component selected from the group consisting of cereal flour, yeast, a chemical leavening agent, a dough strengthening agent, and an emulsifier.

23. A composition according to claim 22 wherein the enzyme is incapable, or substantially incapable, of hydrolyzing both a triglyceride and a 1-monoglyceride.

24. A composition according to claim 22 wherein the enzyme is capable of hydrolyzing a triglyceride and a diglyceride and wherein said enzyme is incapable, or substantially incapable, of hydrolyzing a 1-monoglyceride.

25. A composition according to claim 22 wherein said composition comprises a further enzyme selected from the group consisting of a lipase, a starch degrading enzyme, a hemicellulase, a cellulase, and an oxidoreductase.

26. A dough obtainable by the method according to claim 1.

27. A dough according to claim 26 wherein said dough is frozen or packaged in a controlled atmosphere.

28. A baked product obtainable by baking a dough according to claim 26.

29. A noodle product made from a dough according to claim 26.

30. A pasta product made from a dough according to claim 26.

31. A dough composition comprising an enzyme that, under dough conditions, is capable of hydrolyzing a glycolipid and a phospholipids, wherein said enzyme is incapable, or substantially incapable, of hydrolyzing a triglyceride and/or a 1-monoglyceride.

32. The method of claim 8 wherein the cereal oil comprises oat oil.

* * * * *

UNITED STATES PATENT AND TRADEMARK OFFICE
CERTIFICATE OF CORRECTION

PATENT NO.       : 6,967,035 B2
APPLICATION NO.  : 10/150429
DATED            : November 22, 2005
INVENTOR(S)      : Kirsten Bojsen et al.

Page 1 of 1

It is certified that error appears in the above-identified patent and that said Letters Patent is hereby corrected as shown below:

Column 58, lines 53-54, after "A method according to claim 8 wherein the vegetable oil is naturally occurring cereal" "oll" should read --oil--.

Signed and Sealed this

Twenty-sixth Day of September, 2006

JON W. DUDAS
*Director of the United States Patent and Trademark Office*